(12) United States Patent
Barakat et al.

(10) Patent No.: US 10,905,505 B1
(45) Date of Patent: Feb. 2, 2021

(54) ROBOTIC SURGICAL MANIPULATION SYSTEMS AND METHODS

(71) Applicant: MEMORIAL SLOAN KETTERING CANCER CENTER, New York, NY (US)

(72) Inventors: Richard Barakat, Muttontown, NY (US); Paul Booth, New York, NY (US); Charles Kim, Lewisburg, PA (US); Kelsey Ann Tacca, Munich (DE); Jordan Anthony Rivera, Fairport, NY (US); Samuel Thomas Pratt, Hudson, OH (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 76 days.

(21) Appl. No.: 15/495,316

(22) Filed: Apr. 24, 2017

Related U.S. Application Data

(60) Provisional application No. 62/326,319, filed on Apr. 22, 2016.

(51) Int. Cl.
*A61B 34/35* (2016.01)
*A61B 34/30* (2016.01)
*A61B 34/37* (2016.01)
*A61B 34/00* (2016.01)

(52) U.S. Cl.
CPC ............. *A61B 34/35* (2016.02); *A61B 34/25* (2016.02); *A61B 34/30* (2016.02); *A61B 34/37* (2016.02); *A61B 34/74* (2016.02); *A61B 2034/305* (2016.02); *A61B 2034/742* (2016.02)

(58) Field of Classification Search
CPC ................... A61B 34/30; A61B 34/37; A61B 2017/00477; A61B 2017/2929; A61B 2017/00261; A61B 2017/00327; A61B 2017/0069; A61B 2017/00973; A61B 34/35; A61B 34/71; A61B 34/76; A61B 34/70; A61B 34/74; A61B 34/00; A61B 34/25; A61B 34/72; A61B 2034/305; A61B 2034/301; A61B 17/00234; A61B 17/29; A61B 17/0218; A61B 18/1445; A61B 1/00149; A61B 1/008; A61B 1/00087; A61B 1/3132
See application file for complete search history.

(56) References Cited

U.S. PATENT DOCUMENTS

| | | | |
|---|---|---|---|
| 8,845,622 | B2 | 9/2014 | Paik et al. |
| 8,961,499 | B2 | 2/2015 | Paik et al. |
| 8,989,844 | B2 | 3/2015 | Cinquin et al. |
| 9,375,206 | B2 | 6/2016 | Vidal et al. |
| 9,655,499 | B2 | 5/2017 | Erden et al. |
| 9,700,337 | B2 | 7/2017 | Vidal et al. |
| 9,895,197 | B2 | 2/2018 | Poquet et al. |

(Continued)

OTHER PUBLICATIONS

Akrivos N and Barton-Smith P. A pilot study of robotic uterine and vaginal vault manipulation: the ViKY Uterine Positioner™. J Robot Surg. Dec. 2013; 7(4): 371-5.

*Primary Examiner* — Mohamed G Gabr
(74) *Attorney, Agent, or Firm* — Stroock & Stroock & Lavan LLP

(57) ABSTRACT

The present invention provides, in various embodiments, systems and methods for robotic manipulation of a patient's anatomy, such as the uterus, during minimally invasive surgical procedures.

17 Claims, 25 Drawing Sheets

(56) References Cited

U.S. PATENT DOCUMENTS

| | | | |
|---|---|---|---|
| 2010/0228264 A1* | 9/2010 | Robinson | A61B 18/1206 606/130 |
| 2012/0124743 A1* | 5/2012 | Hensley | A61G 7/0528 5/600 |
| 2014/0188091 A1 | 7/2014 | Vidal et al. | |
| 2015/0032126 A1* | 1/2015 | Nowlin | A61B 34/37 606/130 |
| 2017/0303957 A1 | 10/2017 | Vidal et al. | |
| 2018/0028269 A1 | 2/2018 | Morel et al. | |

* cited by examiner

ROBOTIC SURGICAL MANIPULATION SYSTEMS AND METHODS

RELATED APPLICATIONS

This application claims the benefit of U.S. Provisional Application No. 62/326,319, filed Apr. 22, 2016, which is incorporated herein by reference in its entirety.

BACKGROUND

In gynecologic surgical procedures such as hysterectomies, the patient's uterus needs to be positioned precisely according to the specific requirements of the case throughout the surgery. Improved systems and methods for uterine manipulation are needed in the art.

SUMMARY

The present disclosure relates generally to robotic surgical manipulation systems and methods, and more specifically, to robotic uterine manipulation systems and methods for use in minimally invasive hysterectomies.

In various embodiments, the invention provides a robotic anatomical manipulation system for use with an end effector configured to position and hold an anatomy of a patient during a minimally invasive surgical procedure, the system comprising a remote machine comprising a base comprising a mobile base having one or more lockable casters or a mountable base configured to be mounted to a surgical table, and a moveable extension arm connected to the base, the extension arm having a distal end positionable relative to the surgical table and configured to connect to the end effector; and a control console in communication with the remote machine via a wired connection or a wireless connection. The remote machine is configured to move the end effector responsive to user input received from the control console via the wired connection or the wireless connection. The end effector movement includes translational movement up, down, left, right, in and out, and rotational movement counterclockwise and clockwise.

In some embodiments, the anatomy is a uterus and the minimally invasive surgical procedure is a robotically-assisted or manual laparoscopic hysterectomy.

In some embodiments, the remote machine comprises an articulating joint at the distal end of the extension arm, the articulating joint providing X, Y, and Z translation and Θ, Φ, and Ψ rotation of the end effector.

In some embodiments, the articulating joint comprises a translating surface at a proximal end of the articulating joint, a linear actuator at a distal end of the articulating joint, a plurality of linear actuators with distal ends mounted to a pivoting surface, and a rotating surface mounted to a distal end of either the pivoting surface or the translating surface.

In some embodiments, the remote machine comprises a mobile base having a vertical extension joint for adjusting the elevation of the extension arm, a horizontal extension joint for moving the extension arm laterally, and a foot control panel to lock and unlock the casters. In some embodiments, the remote machine comprises an articulating joint at the distal end of the extension arm, the articulating joint providing X, Y, and Z translation and Θ, Φ, and Ψ rotation of the end effector. In some embodiments, the remote machine comprises a local control panel configured to control the mobile base caster locks, the vertical and horizontal extension joints, and the articulating joint, and to perform startup sequences, calibration, and operation.

In some embodiments, the remote machine comprises a mobile base having a bumper bar configured to be raised and lowered to lock and unlock the casters. In some embodiments, the extension arm comprises two linear segments comprising a proximal segment and a distal segment, a first Ψ rotation joint and a first Φ rotation joint at a proximal end of the proximal segment connected to the mobile base, a second Φ rotation joint between the proximal and distal segments, a second Ψ rotation joint and a third Φ rotation joint at a distal end of the distal segment, and a Θ rotation joint and a translation extension joint connected to the interface.

In some embodiments, the remote machine comprises a mountable base having a vertical extension joint for adjusting the elevation of the extension arm, a horizontal extension joint for moving the extension arm laterally, and a Ψ rotation joint for rotating the extension arm toward and away from the surgical table. In some embodiments, the extension arm comprises a first Θ rotation joint at a proximal end of the extension arm, a Φ rotation joint at the distal end of the extension arm, and a second Θ rotation joint connected to the interface. In some embodiments, the remote machine comprises an articulating joint at the distal end of the extension arm, the articulating joint providing X, Y, and Z translation and Θ, Φ, and Ψ rotation of the end effector. In some embodiments, the remote machine comprises a local control panel configured to control the mobile base caster locks, the vertical and horizontal extension joints, and the articulating joint, and to perform startup sequences, calibration, and operation.

In some embodiments, the remote machine comprises a mountable base having a Ψ rotation joint for rotating the extension arm toward and away from the surgical table. In some embodiments, the extension arm comprises a horizontal arc and a vertical arc, a translation arc nesting extension joint for moving the horizontal arc laterally along a horizontal curve, and a vertical translation arc track having a vertical gantry on its underside for adjusting the elevation of the vertical arc along a vertical curve. In some embodiments, the remote machine comprises an articulating joint at the distal end of the extension arm, the articulating joint providing X, Y, and Z translation and Θ, Φ, and Ψ rotation of the end effector. In some embodiments, the remote machine comprises a local control panel configured to control the mobile base caster locks, the vertical and horizontal extension joints, and the articulating joint, and to perform startup sequences, calibration, and operation.

In some embodiments, the remote machine comprises a mobile base having a curved vertical extension arm protruding from the top of the mobile base, a horizontal track for moving the extension arm laterally, and a vertical translation arc track having a vertical gantry on its underside for adjusting the elevation of the extension arm along a vertical curve. In some embodiments, the remote machine comprises an articulating joint at the distal end of the extension arm, the articulating joint providing X, Y, and Z translation and Θ, Φ, and Ψ rotation of the end effector. In some embodiments, the remote machine comprises a local control panel configured to control the mobile base caster locks, the vertical and horizontal extension joints, and the articulating joint, and to perform startup sequences, calibration, and operation.

In some embodiments, the remote machine further comprises an interface connected to the distal end of the extension arm, the interface configured to connect to the end effector.

Additional features and advantages of the present invention are described further below. This summary section is meant merely to illustrate certain features of the invention, and is not meant to limit the scope of the invention in any way. The failure to discuss a specific feature or embodiment of the invention, or the inclusion of one or more features in this summary section, should not be construed to limit the invention as claimed.

BRIEF DESCRIPTION OF THE DRAWINGS

The foregoing summary, as well as the following detailed description of the preferred embodiments of the application, will be better understood when read in conjunction with the appended drawings. For the purposes of illustrating the systems and methods of the present application, there are shown in the drawings preferred embodiments. It should be understood, however, that the application is not limited to the precise arrangements and instrumentalities shown. In the drawings.

DETAILED DESCRIPTION

In a minimally invasive (robotic-assisted or manual laparoscopic) gynecologic surgery such as a hysterectomy, the patient's uterus needs to be positioned precisely according to the specific requirements of the case throughout the surgery. Uterine manipulation is an important component of a successful minimally invasive hysterectomy, wherein the anatomy is manipulated to tilt the uterus forward and back and/or displace it laterally for safe dissection of the ureter, suspensory ligaments of the uterus, and the uterine blood supply.

The current standard of practice is for a surgical resident or fellow, taking positional instructions from the operating surgeon, to manipulate the uterus manually using one or more handheld tools. Over the course of the surgery, this practice can present significant physical demands, as the resident or fellow often has to maneuver themselves around other equipment used in the surgery, such as the large footprint of a surgical robot. This practice can be difficult, as the individual manipulating the uterus may be situated at an awkward angle or to the side of the perineum. It can also be physically demanding.

The present invention overcomes such problems and provides, in various embodiments, robotic anatomical manipulation systems and methods, which can provide more accurate and precise manipulation and positioning of the anatomy, as compared to the current standard of practice. Using the robotic anatomical manipulation systems and methods of the present invention, the surgeon can control the position of the anatomy from a control console away from the operating table. The surgeon can more precisely adjust the instruments and the anatomy of the patient to exactly the desired positions and can yield a superior surgical result.

System Architecture

Figure 1:
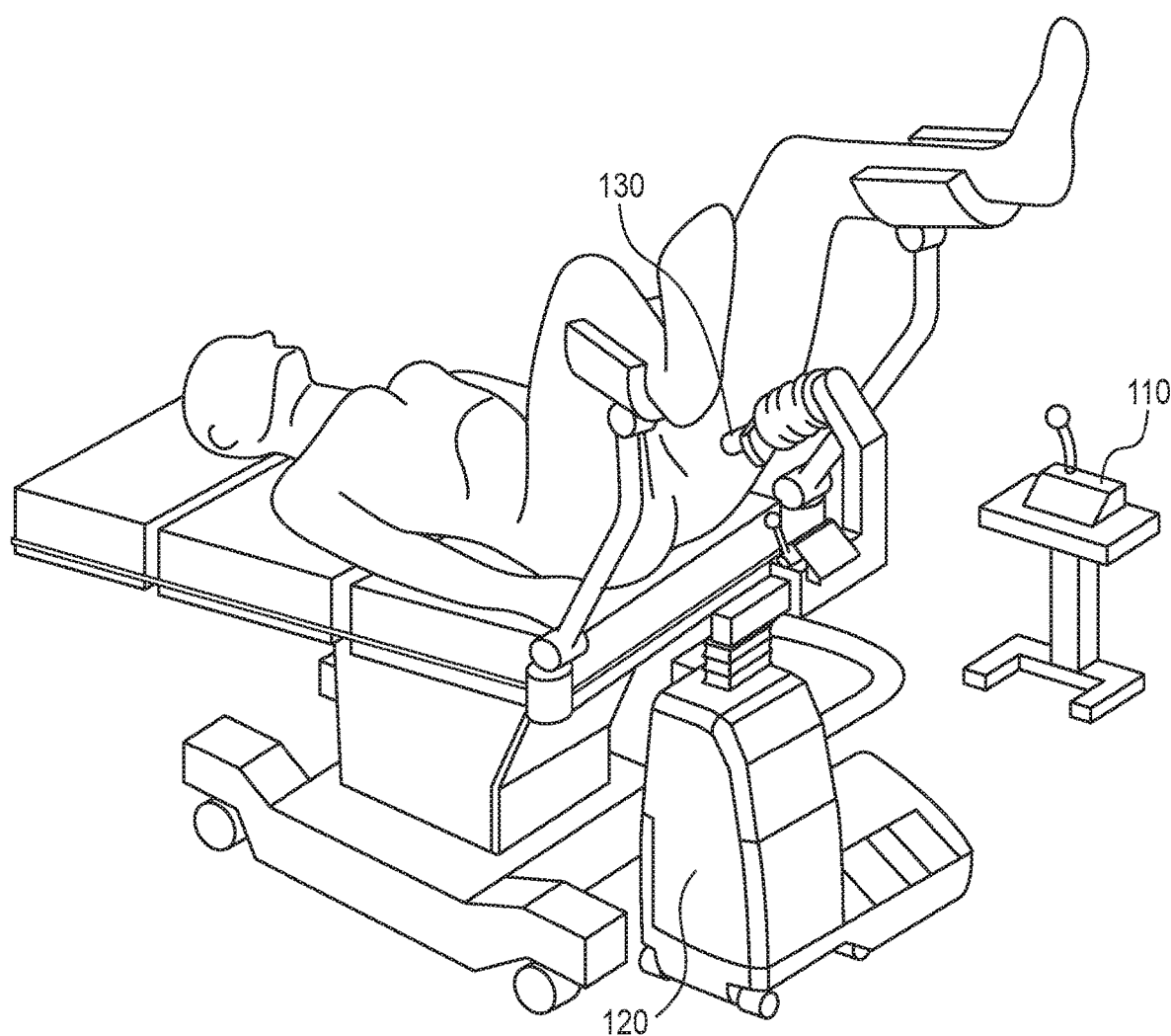
FIG. 1 is a schematic diagram of an exemplary robotic uterine manipulation system, according to some embodiments of the invention.

In various embodiments, the invention provides robotic uterine manipulation systems as shown schematically in FIG. 1, comprising a control console 110 away from the operating table (either positioned nearby as shown, or located remotely) and a remote machine 120 at the foot of the operating table, with an interface 130 to which an end effector can be attached.

Figure 2:
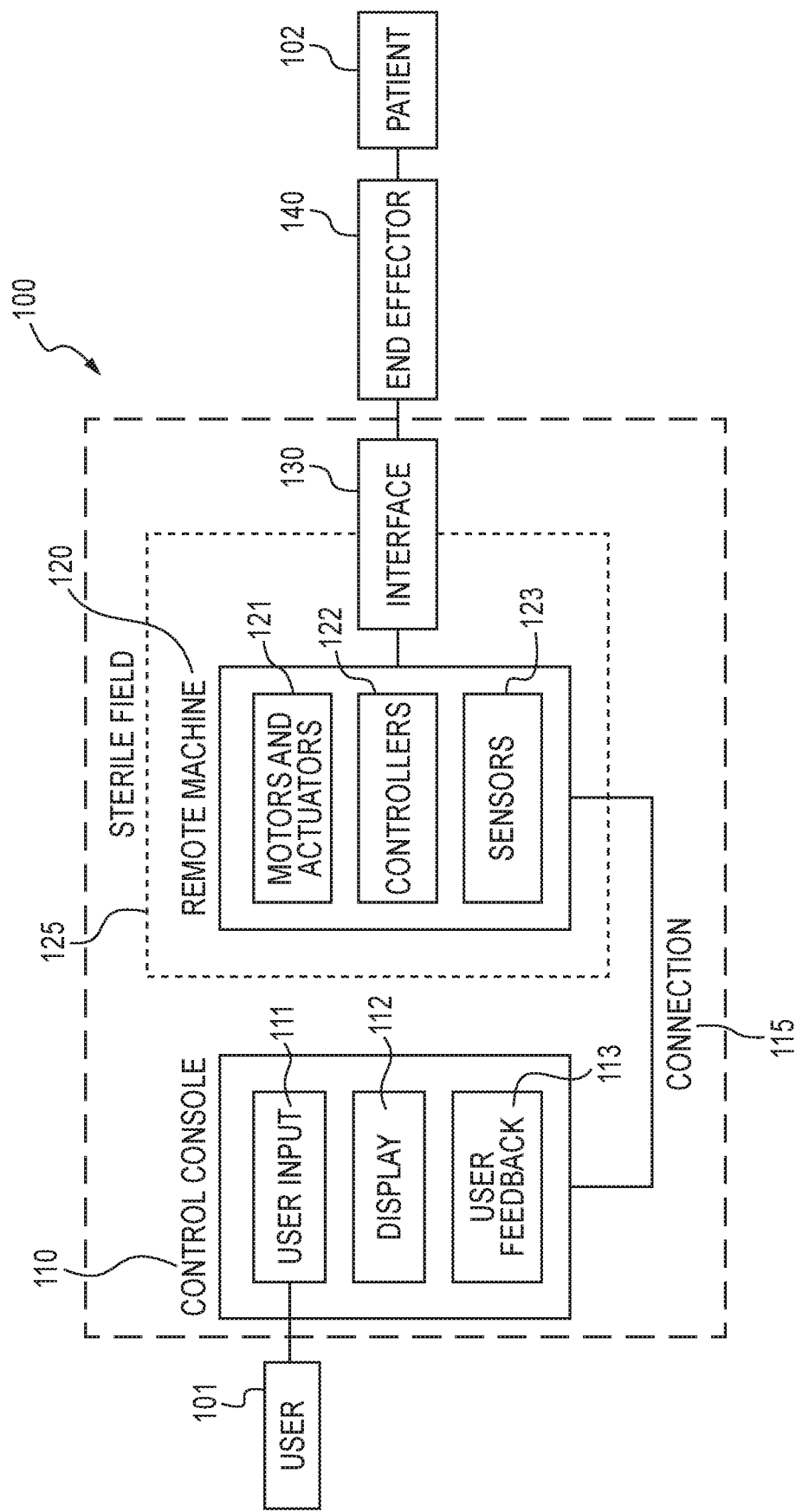
FIG. 2 is a schematic diagram of a system architecture for an exemplary robotic uterine manipulation system, according to some embodiments.

With reference to FIG. 2, an exemplary robotic uterine manipulation system 100 according to the present invention (inside dashed lines) comprises a control console 110, a remote machine 120, and an optional interface 130, which is an adapter for connecting different end effectors to the remote machine 120. System 100 responds to control input 111 from a user 101 (e.g., the surgeon performing the hysterectomy), manipulates the uterus via an end effector 140 inserted through the vagina, and provides feedback (e.g., graphical or audio) via a feedback interface 113 to the user 101 based on, for example, sensors 123.

Remote Machine

In some embodiments, as shown in FIG. 1 and described in more detail below, the remote machine 120 comprises a mobile or stationary platform located at the foot of the surgical table, although other positions are within the scope of the invention. For example, in further embodiments, the remote machine 120 may comprise a mobile or stationary platform located on either side of the surgical table, or a mobile or stationary platform located at the head of the surgical table (for procedures other than a hysterectomy). In other embodiments, as described in more detail below, the remote machine 120 may be configured to be mounted to the foot of the surgical table although other mounting points are within the scope of the invention. For example, in further embodiments, the remote machine 120 may be configured to be mounted to either side of the surgical table, or may be configured to be mounted to the head of the surgical table (for procedures other than a hysterectomy).

The remote machine 120 interfaces, via interface 130, with an end effector 140, which is an interchangeable tool that interfaces with the patient 102 on the surgical table. For example, the interface 130 may include a permanent or releasable fastening means, such as one or more threaded components, screws/screw holes, clasps, or other mechanical, electro-mechanical, magnetic or combination means, that couples with (directly or indirectly) various end effectors, which may reusable or disposable. Different end effectors for manipulating different anatomies may be used with different surgical procedures, such as gastrointestinal surgeries and rectal surgeries. For the gynecologic surgical procedures described herein, the end effector 140 may be a uterine manipulator comprising a cervical cup. An exemplary end effector is the VCare® uterine manipulator (CONMED, Utica, N.Y.). In other embodiments, different end effector devices may be selected by the surgeon based on the patient and the needs of each surgery (e.g., selection of different sizes or types). Existing end effectors may be adapted for use with the remote machine 120 and/or new end effectors (reusable and/or single use) may be developed for use with the remote machine 120.

Preferably, a sterile field (inside dotted lines) is maintained between the patient 102 and the remote machine 120, where the interface 130 serves as a transition to the sterile field. In some embodiments, the sterile field may be maintained by a disposable sterile drape 125, which can cover the remote machine 120 and all or part of the interface 130. In other embodiments, the remote machine 120 may be sterile, and means for maintaining a sterile field are not required.

The remote machine 120 encloses motors/actuators 121, controllers 122 (e.g., one or more processors), and sensors 123 configured to manipulate the end effector 140 based on user instructions. The remote machine 120 can be powered from a local power source, powered from the control console 110, or powered from onboard energy storage. In some embodiments, the logic and processors to translate the user inputs 111 into motions of the end effector 140 and to process the sensor feedback are located within the remote machine 120. The logic and processors can be provided in various formats such as, but not limited to, desktop computer workstations, laptop computers, embedded processors, and third-party industrial control systems. The logic and processing power can reside solely within the remote machine 120, solely within the control console 110, or can be distributed and shared between the remote machine 120 and the control console 110.

The remote machine 120 receives control inputs 111 from and transmits sensor data and information to the control console 110 via a connection 115. The control inputs 111 can comprise raw input control signal, processed motor control commands, or high-level instruction. The sensor data can comprise raw uncalibrated sensor output, raw calibrated sensor data, integrated sensor information, and/or high-level description. In some embodiments, the connection 115 can comprise a physical connection such as, but not limited to, a cable which has individual control wires or one or more wires used in a communication protocol such as, but not limited to, TCP, serial, ModBus, and ProfiBus. Various known communication methodologies can be used for a wired connection between the remote machine 120 and the control console 110. In other embodiments, the connection 115 may comprise a wireless connection between the remote machine 120 and the control console 110. Various known wireless communication protocols can be used for a wireless connection between the remote machine 120 and the control console 110 including, but not limited to, cellular, wireless TCP, and Bluetooth®.

In some embodiments, the remote machine 120 can determine (e.g., via sensors 123) how much force is applied to the working end. The force may be determined by various methods, for example, by measuring current on the respective motors, by a force sensor engaged as part of the end effector 140, by a force sensor engaged as part of the extension arm of the remote machine 120 to which the end effector 140 is attached, or by a force sensor integrated into the interface 130. Force levels can be customizable, for example, set by the surgeon around their preference based on clinical requirements. Reactions to a force overload (e.g., exceeding a stored threshold or limit value) condition may be provided (warning tones, lights, text indications, etc.), which may or may not automatically stop the remote machine 120. In embodiments where the remote machine 120 is automatically stopped as a result of force overload, controls may be provided in the console 110 for surgeon override.

For safety, the remote machine 120 is fail-safe and can be removed safely from the patient 102 in either a powered or an unpowered mode.

While the exemplary embodiments of the remote machine 120 described herein (detailed further below) are constructed and arranged to facilitate gynecologic surgical procedures, different end effectors and/or remote machine configurations/designs could be used in other embodiments without departing from the spirit of the invention, such as, but not limited to, static designs, designs with energy delivery (electrosurgical units), designs with sensor probes (ultrasound, temperature, etc.), designs with lighting, and designs with optics and cameras.

Control Console

In some embodiments, as shown in FIG. 1, the control console 110 is a mobile or stationary platform separate from (located in proximity to or located remotely from) the remote machine 120. In other embodiments, the control console 110 may be integrated with the remote machine 120.

The control console 110 interfaces with the user 101 via one or more user inputs 111, which may include, but are not limited to, one or more of the following in any combination: joystick, mouse, keyboard, track/touch pad, stylus, touchscreen, voice control, and hands-free input device such as a motion tracking system.

The control console 110 provides data and information about the control console 110 and the remote machine 120 via a feedback interface 113 and a display 112. The display 112 provides visual information to the user. The visual information can include feedback information from the remote machine 120 regarding system status and end effector 140 position. The visual information can also include video from external sources such as surgical camera feeds. In various embodiments, the display 112 can provide a visual presentation of information on the control console 110 including monitors, lights, dials, gauges, a remote visual presentation of information sent from the control console 110 to an external display device such as a computer monitor or television, or a visual presentation of information to a personal device such as virtual reality glasses, cell phone, or personal computer. In some embodiments, in addition to display 112 information, non-visual information can be provided by one or more audio devices such as, but not limited to, buzzers or speakers and/or haptic-feedback such as vibrations in the user input 111 devices or other equipment. The audio feedback can provide alerts and alarms from the system 100 regarding system status and end effector 140 position. The audio feedback can also provide audio from external sources such as surgical camera/microphone feeds.

The control console 110 can be powered from a local power source, powered from the remote machine 120, or powered from onboard energy storage. In some embodiments, the logic and processors to translate the user inputs 111 into motions of the end effector 140 and to process the sensor feedback are located within the control console 110. The logic and processors can be provided in various formats such as, but not limited to, desktop computer workstations, laptop computers, embedded processors, and third-party industrial control systems. The logic and processing power can reside solely within the remote machine 120, solely within the control console 110, or can be distributed and shared between the remote machine 120 and the control console 110.

In some embodiments, the control console 110 and the remote machine 120 are combined in the same physical enclosure, and the user 101 can control the remote machine 120 directly, with the connection 115 existing internally within the joint enclosure.

Remote Machine—First Embodiment

Figure 25:
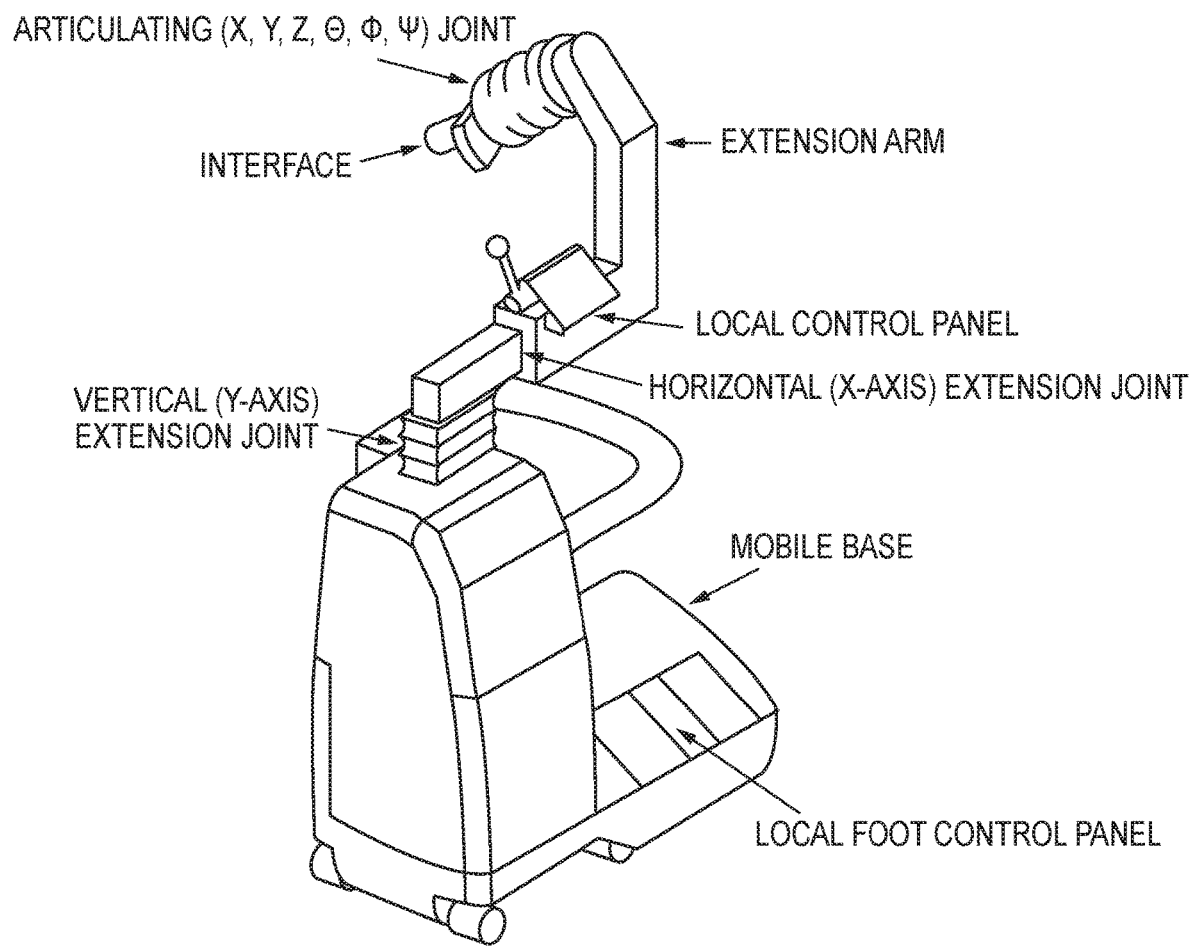
FIGS. 25-31 are schematic diagrams of different exemplary remote machines and interfaces, according to various embodiments.

A first embodiment of the remote machine, shown in FIG. 25, is configured to be positioned at the foot of the surgical table as shown schematically in FIG. 1. The remote machine has a mobile base. The mobile base allows the remote machine to be positioned as appropriate. The mobile base has lockable casters. The mobile base has a foot control panel to lock and unlock the casters as well as perform coarse positioning of the interface point.

The remote machine has a vertical extension joint for raising and lowering the remote machine interface to position the interface at the proper elevation given the height of the surgical table and the anatomy of the patient. The vertical extension joint is a linear actuator.

The remote machine has a horizontal extension joint for translating the remote machine interface to position the interface at the proper lateral position given the position of the mobile base, relative to the surgical table, the patient on the surgical table, and the anatomy of the patient. The horizontal extension joint is a linear actuator.

The mobile base, vertical extension joint, and horizontal extension joint are used to position and align the remote machine interface point with the patient's anatomy prior to the start of the surgical procedure.

The remote machine has an articulating joint at the end of the extension arm. The articulating joint allows for X, Y and Z translation as well as $\Phi$, $\Phi$, and $\Psi$ rotation of the interface point. The articulating joint is used during the surgery to manipulate the end effector connected to the interface to manipulate the patient's uterus or other anatomy. The articulating joint is described in further detail below.

The remote machine has an interface that couples the articulating joint to the end effector. The interface can accommodate one or more different end effectors. The interface is replaceable and different interfaces can connect to the articulating joint to accommodate different end effectors.

The remote machine has a local control panel for control of the mobile base caster locks, vertical and horizontal extension joints, and the articulating joint. The local control panel can perform startup sequences, calibration, and operation.

Figure 27:
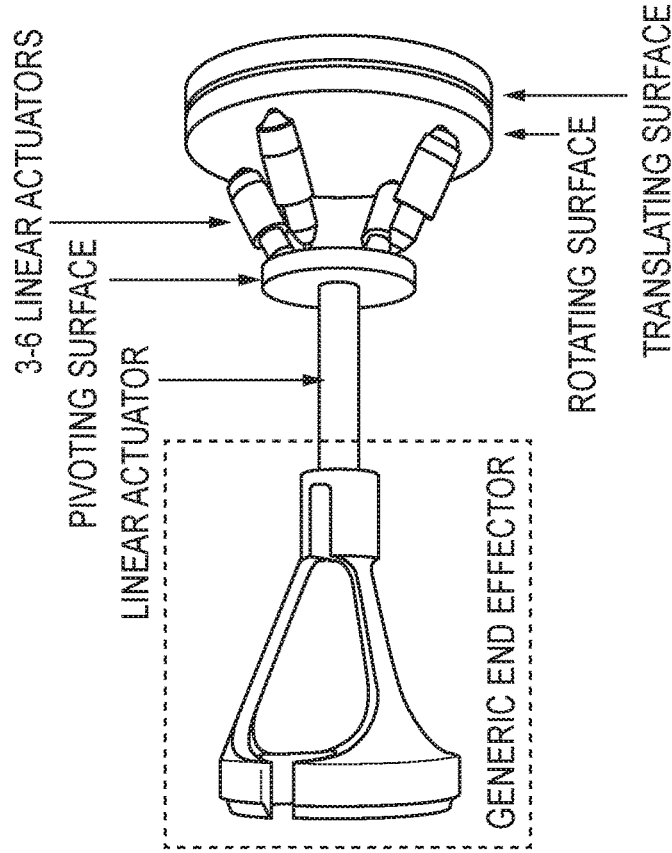
Figure 26:
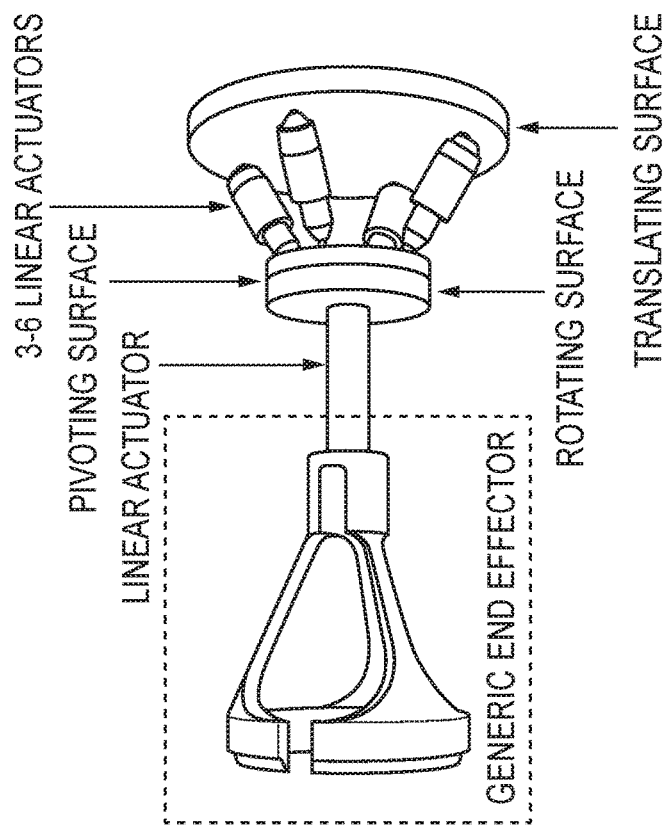

The articulating joint at the end of the extension arm can be an articulating x-pod having between three and six pivot-mounted linear actuators. FIGS. 26 and 27 show exemplary articulating x-pods each having four linear actuators mounted to a pivoting surface (quadrapods). The x-pod provides translation and pivoting of the pivoting surface. A rotating surface is provided, which can be connected at the top of the x-pod as shown in FIG. 26 or at the base of the x-pod as shown in FIG. 27. A linear actuator is attached to the top of the x-pod, and the end effector attaches to the articulating joint at an interface (not shown in FIGS. 26 and 27).

Remote Machine—Second Embodiment

Figure 28:
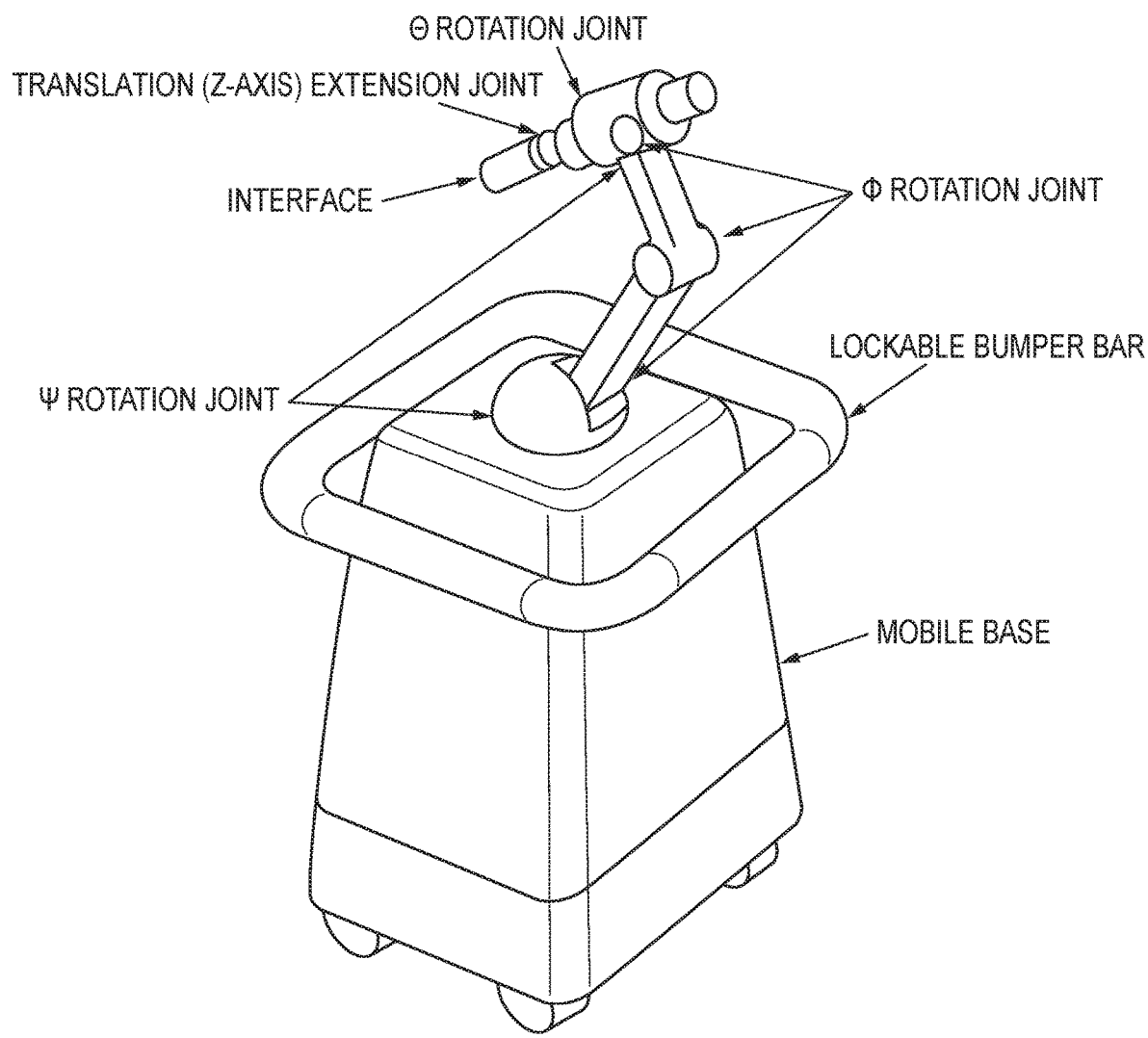

A second embodiment of the remote machine, shown in FIG. 28, is configured to be positioned at the foot of the surgical table. The remote machine has a mobile base. The mobile base allows the remote machine to be positioned as appropriate. The mobile base has lockable casters. The mobile base has a bumper bar that is raised or lowered to lock and unlock casters.

The mobile base has a $\Psi$ rotation joint and a $\Phi$ rotation joint connecting to the arm. The arm is composed of two linear segments. The lower arm segment connects to the joint connected to the mobile base and to another $\Phi$ rotation joint. The upper arm segment connects the same $\Phi$ rotation joint as the top of the lower arm segment. The top of the upper arm segment connects to a third $\Phi$ rotation joint and a $\Psi$ rotation joint. The interface connects to the upper arm segment through a $\Theta$ rotation joint.

The combination of the three $\Phi$ rotation joints, two $\Psi$ rotation joints, one $\Theta$ rotation joint, and one translational extension joint provides the articulation j used during the surgery to manipulate the end effector connected to the interface to manipulate the patient's uterus or other anatomy.

The remote machine has an interface that couples the $\Theta$ rotation joint and translational extension joint to the end effector. The interface can accommodate one or more different end effectors. The interface is replaceable and different interfaces can connect to the remote machine to accommodate different end effectors.

Remote Machine—Third Embodiment

Figure 29:
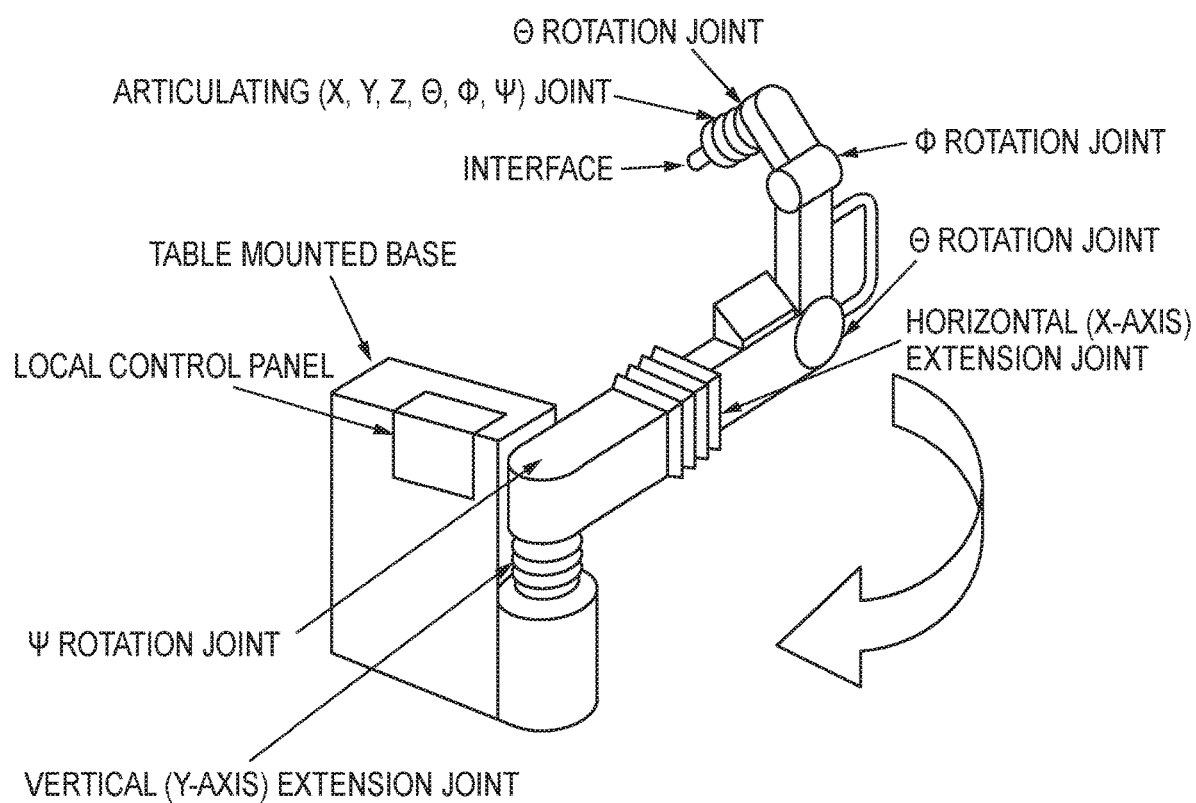

A third embodiment of the remote machine, shown in FIG. 29, is configured to be mounted. The remote machine has a base mounted to the surgical table. The remote machine is hand carried or loaded on a cart for transportation and attachment to the surgical table.

The remote machine has a vertical extension joint for raising and lowering the remote machine interface to position the interface at the proper elevation given the height of the surgical table and the anatomy of the patient. The vertical extension joint is a linear actuator.

The remote machine has a horizontal extension joint for translating the remote machine interface to position the interface at the proper lateral position given the position of the mobile base, relative to the surgical table, the patient on the surgical table, and the anatomy of the patient. The horizontal extension joint is a linear actuator.

The remote machine has a $\Psi$ rotation joint for rotating the arm toward or away from the surgical table and patient.

The remote machine has a $\Theta$ rotation joint and a $\Phi$ rotation joint for rotating the remote machine interface to position the interface at the proper lateral position given the position of the mobile base, relative to the surgical table, the patient on the surgical table, and the anatomy of the patient.

The mobile base, vertical extension joint, and horizontal extension joint are used to position and align the remote machine interface point with the patient's anatomy prior to the start of the surgical procedure.

The remote machine has an articulating joint at the end of the extension arm. The articulating joint allows for X, Y, and Z translation as well as $\Theta$, $\Phi$, and $\Psi$ rotation of the interface point. The articulating joint is used during the surgery to manipulate the end effector connected to the interface to manipulate the patient's uterus or other anatomy. The articulating joint is further detailed above in the description of the first embodiment remote machine.

The remote machine has an interface that couples the articulating joint to the end effector. The interface can accommodate one or more different end effectors. The interface is replaceable and different interfaces can connect to the articulating joint to accommodate different end effectors.

The remote machine has a local control panel for control of the mobile base caster locks, vertical and horizontal extension joints, and the articulating joint. The local control panel can perform startup sequences, calibration, and operation.

Remote Machine—Fourth Embodiment

Figure 30:
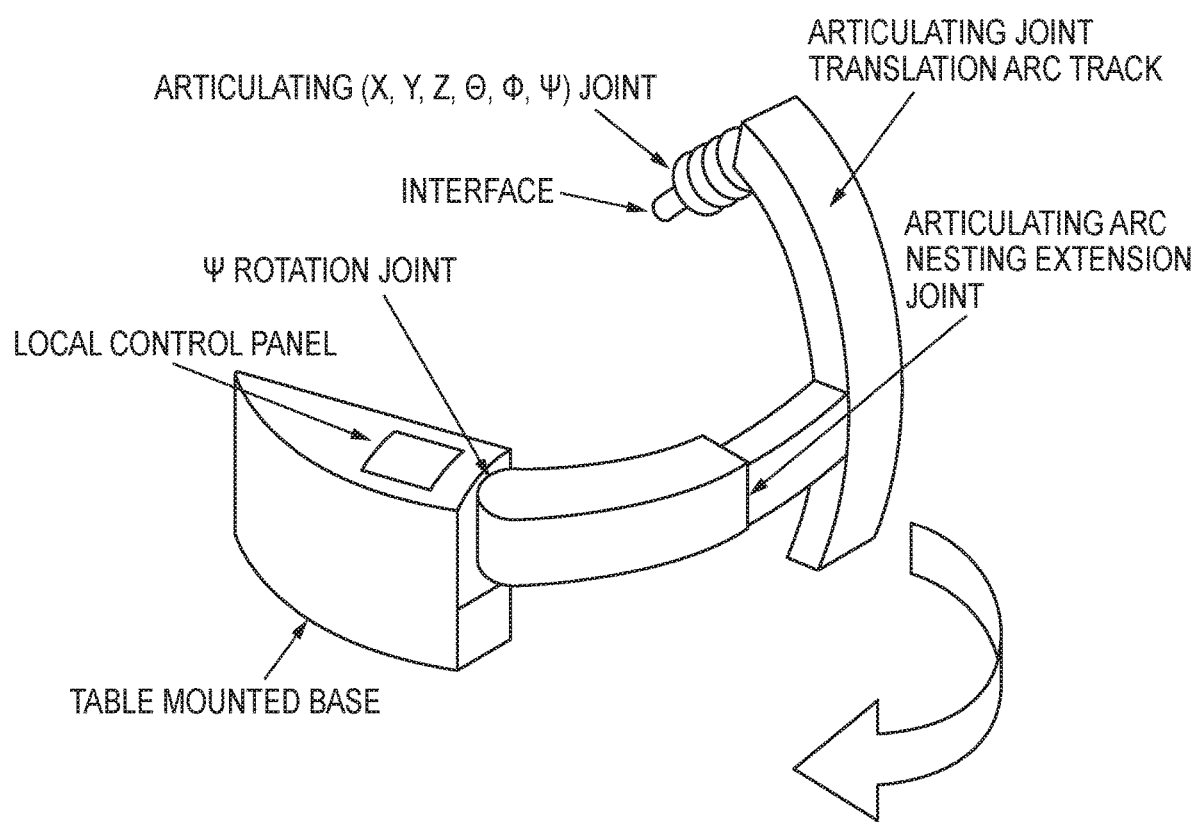

A fourth embodiment of the remote machine, shown in FIG. 30, is configured to be mounted. The remote machine has a base mounted to the surgical table. The remote machine is hand carried or loaded on a cart for transportation and attachment to the surgical table.

The remote machine has a $\Psi$ rotation joint for rotating the arm toward or away from the surgical table and patient.

The remote machine has a translation arc nesting extension joint for translating the remote machine interface to position the interface at the proper lateral position given the position of the mobile base, relative to the surgical table, the patient on the surgical table, and the anatomy of the patient. The translation arc nesting extension joint is a curved linear actuator.

The remote machine has a vertical translation arc track at the end of the horizontal arc extension arm. The underside of the translation arc track has a vertical gantry which allows the articulating joint to raise and lower in a vertical curve.

The remote machine has an articulating joint at the end of the extension arm. The articulating joint allows for X, Y and Z translation as well as $\Theta$, $\Phi$, and $\Psi$ rotation of the interface point. The articulating joint is used during the surgery to manipulate the end effector connected to the interface to manipulate the patient's uterus or other anatomy. The articulating joint is further detailed above in the description of the first embodiment remote machine.

The remote machine has an interface that couples the articulating joint to the end effector. The interface can accommodate one or more different end effectors. The interface is replaceable and different interfaces can connect to the articulating joint to accommodate different end effectors.

The remote machine has a local control panel for control of the mobile base caster locks, vertical and horizontal extension joints, and the articulating joint. The local control panel can perform startup sequences, calibration, and operation.

Remote Machine—Fifth Embodiment

Figure 31:
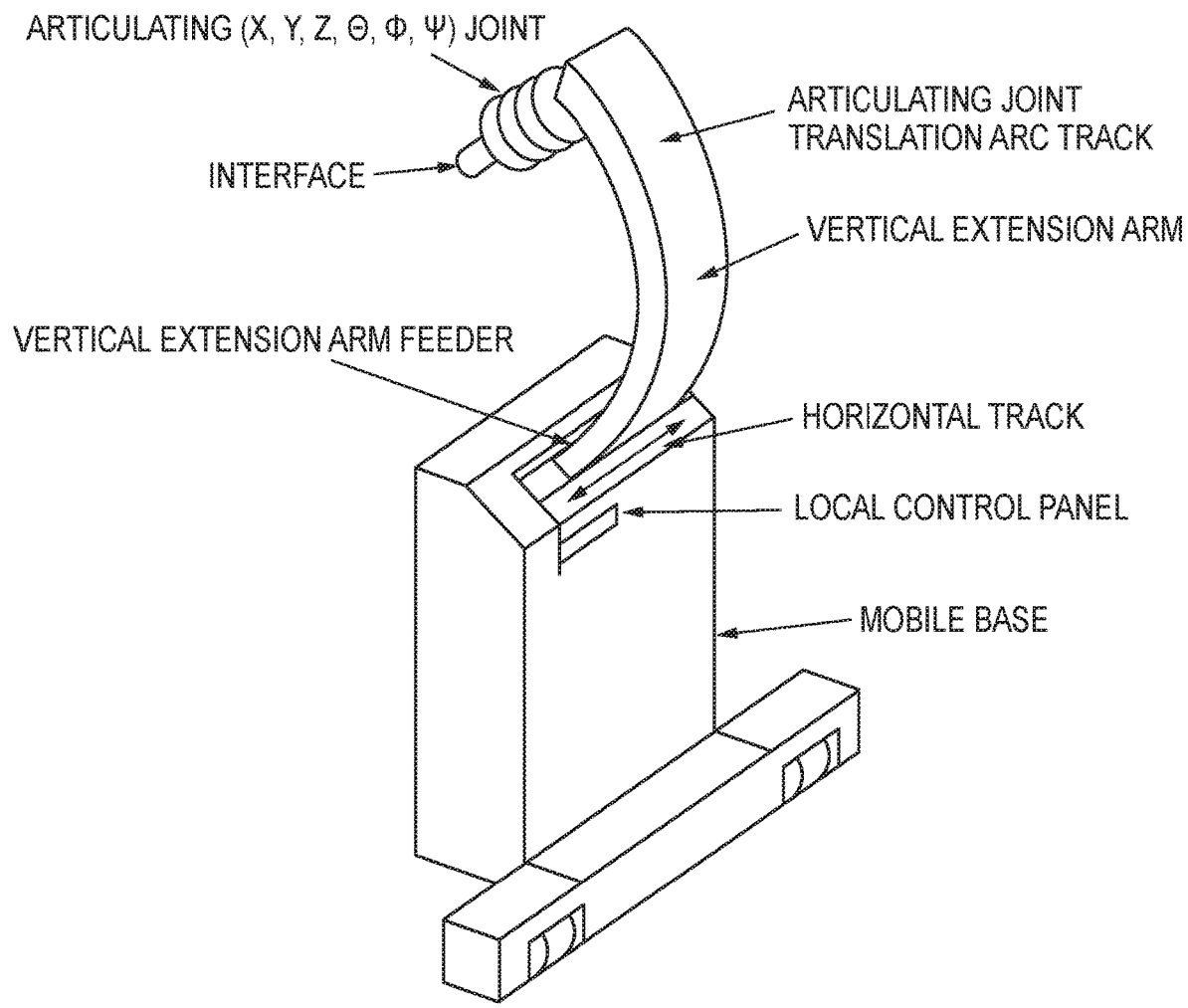

A fifth embodiment of the remote machine, shown in FIG. 31, is configured to be positioned at the foot of the surgical table. The remote machine has a mobile base. The mobile base allows the remote machine to be positioned as appropriate. The mobile base has lockable casters.

The mobile base has a curved vertical extension arm protruding from the top of the base. The vertical extension arm can be moved horizontally to align the interface with the patient relative to the mobile base. The mobile base can extend or retract the vertical extension arm to raise or lower the interface in a curved path to align the interface with the patient.

The remote machine has a vertical translation arc track on the vertical extension arm. The underside of the translation arc track has a vertical gantry which allows the articulating joint to raise and lower in a vertical curve.

The remote machine has an articulating joint at the end of the extension arm. The articulating joint allows for X, Y, and Z translation as well as $\Theta$, $\Phi$, and $\Psi$ rotation of the interface point. The articulating joint is used during the surgery to manipulate the end effector connected to the interface to manipulate the patient's uterus or other anatomy. The articulating joint is further detailed above in the description of the first embodiment remote machine.

The remote machine has an interface that couples the articulating joint to the end effector. The interface can accommodate one or more different end effectors. The interface is replaceable and different interfaces can connect to the articulating joint to accommodate different end effectors.

The remote machine has a local control panel for control of the mobile base caster locks, vertical and horizontal extension joints, and the articulating joint. The local control panel can perform startup sequences, calibration, and operation.

Control Console—First Embodiment

Figure 4A:
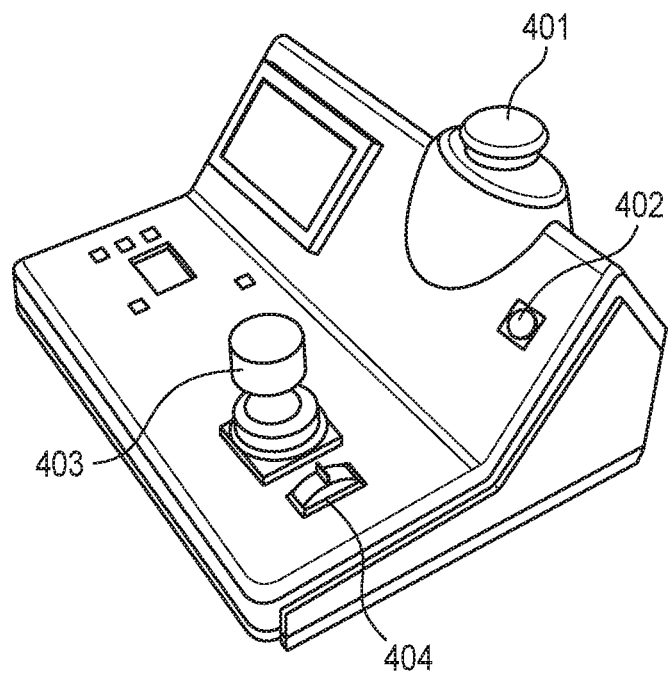
FIGS. 4A and 4B are schematic diagrams of an exemplary control console, according to some embodiments.
Figure 4B:
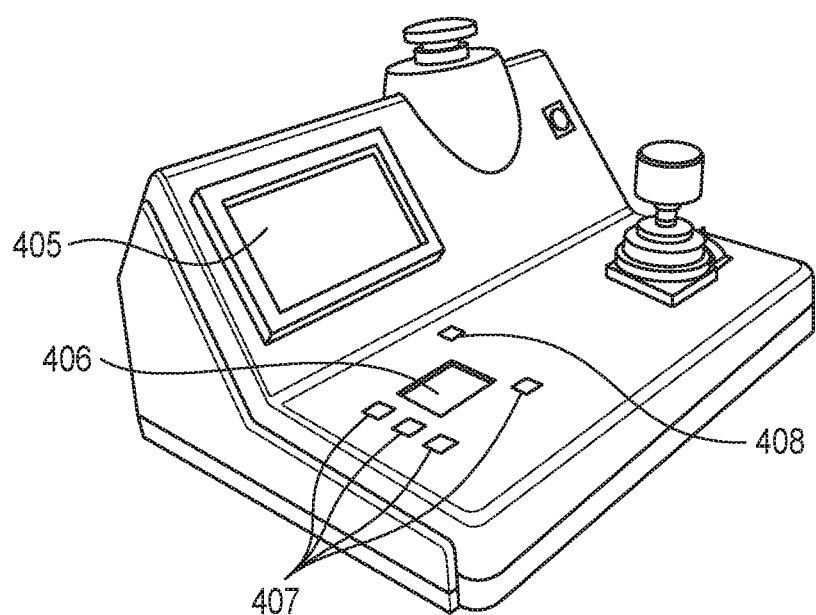

FIGS. 4A and 4B are schematic diagrams of an exemplary control console, according to some embodiments of the invention. The control console includes a power switch 402, which turns the control console on and off, as well as an emergency stop switch 401, which can immediately cut power to the control console, and any equipment connected to the control console. Two control actuators can control translational motion of the end effector up, down, left, right, in, and out, as well as rotational motion of the end effector counterclockwise/left and clockwise/right. For example, a joystick 403 can provide X,Y (up, down, left, right) and rotational (rotate counterclockwise, rotate clockwise) control, and a thumbwheel or rocker switch 404 can provide in/out control. In some embodiments, voice control commands and/or foot control pedals, which may be ineffective and/or inefficient, are not used for motion control. A video display 405 can show the user of the control console a view, for example, from the distal end of the extension arm of the remote machine 120 (e.g., where interface 130 and end effector 140 are attached), and a status display 406 can provide information thereon, such as the relative position (e.g., actual versus full range) and the actual position of the interface 130 and/or the end effector 140. Various control buttons 407 can be included which can be used to control the end effector. A lock button 408 may be provided (e.g., to lock the end effector into the correct position, which position may be stored in memory such that the user can return to such position by, e.g., activating a control button).

In some embodiments, the control console is mounted on a dedicated stand, as shown schematically in FIG. 1. Mounting the control console on a dedicated stand provides high rigidity and stability, and makes the console more robust, as compared to a table-mounted console. In some embodiments, the control console may be permanently mounted to the stand. In other embodiments, the control console may be removeably mounted to the stand.

In some embodiments, a control pad may be provided on the control console, so that the user can identify and store a specific position of the anatomy at any time, move away from that location for clinical needs, and be able to return to the stored location easily.

In some embodiments, the control console may enter a calibration mode when turned on, which can provide an absolute positioning reference of the interface. The calibration process may also serve as a feedback mechanism to ensure that the location of the interface is accurate.

In some embodiments, the control console is not sterile, but is surgically draped for use within a sterile field (e.g., when the user is a surgeon who is scrubbed).

Control Console—Second Embodiment

Figure 32:
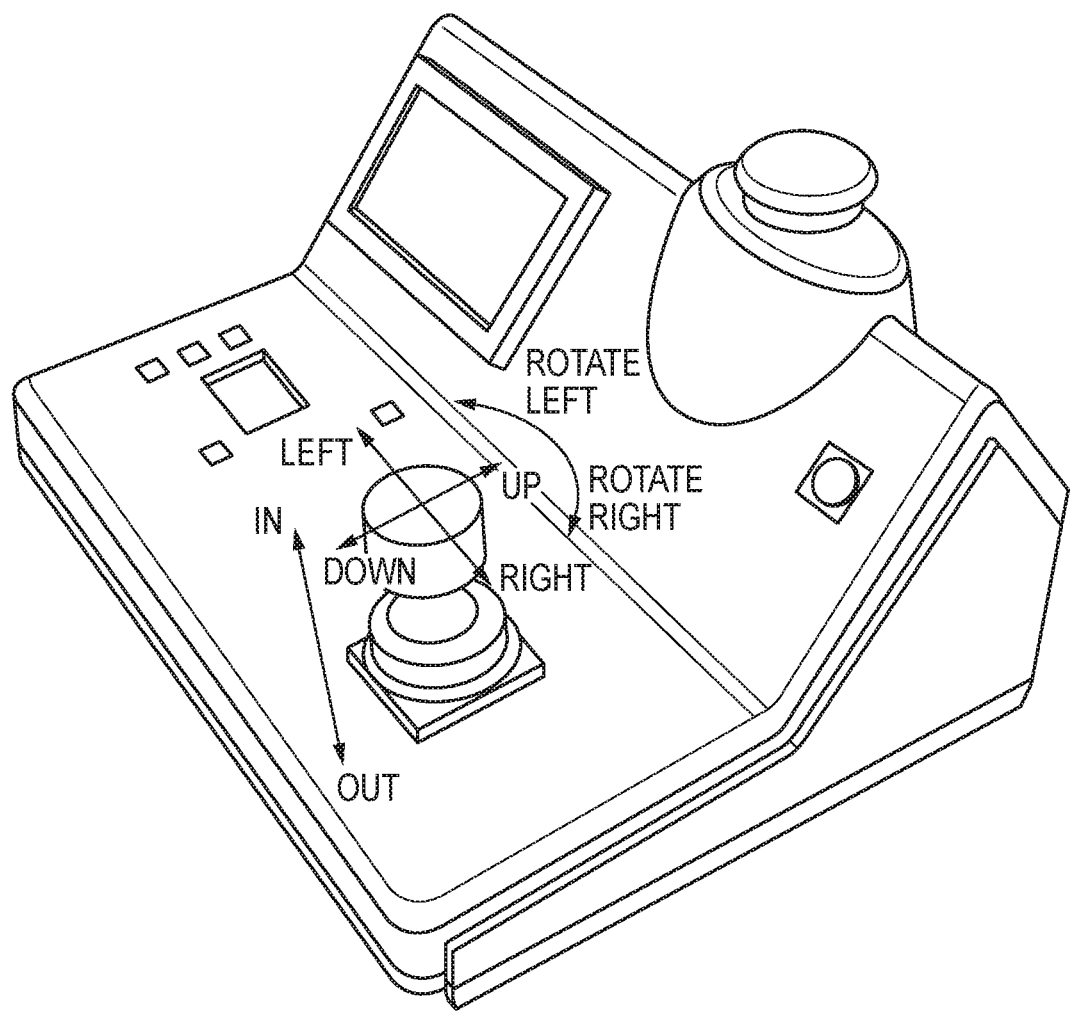
FIG. 32 is a schematic diagram of another exemplary control console, according to some embodiments.

In alternative embodiments, as shown in FIG. 32, the control console may comprise a single control actuator for all movement. For example, an X,Y joystick with rotation and push-in/pull-up capability can provide up, down, left, right, and rotational (counterclockwise and clockwise) control as well as in/out control (provided by the separate rocker in the first embodiment control console).

Exemplary Robotic Uterine Manipulation System

Figure 3:
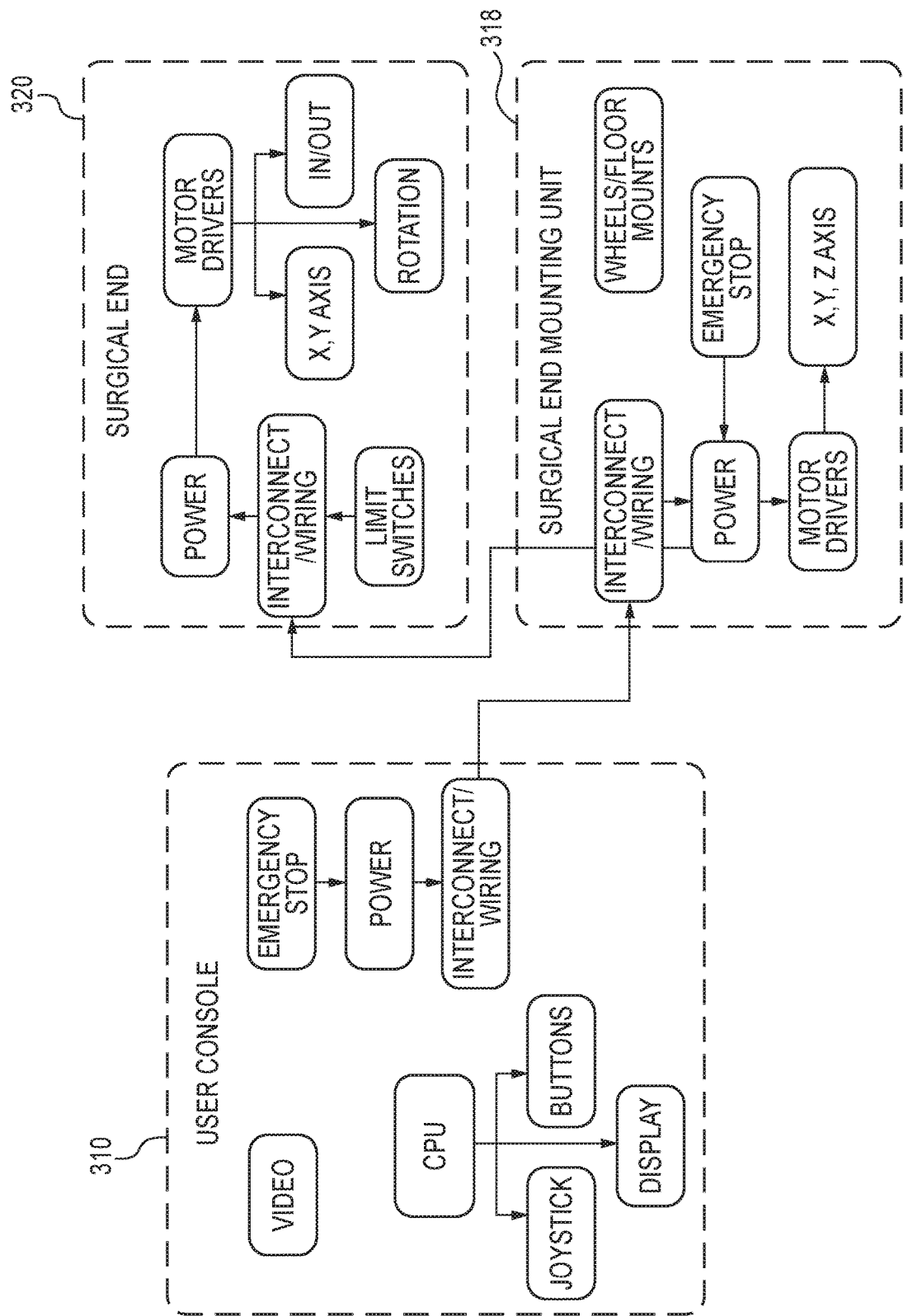
FIG. 3 is a schematic diagram of a system architecture for another exemplary robotic uterine manipulation system, according to some embodiments.

As shown in FIG. 3, in some embodiments, an exemplary robotic uterine manipulation system of the present invention may comprise a user console 310, a surgical end 320, and a surgical end mounting unit 318. The surgical end mounting unit 318 may comprise an exemplary device table as described below, comprising a base with lockable wheels and means for macro X, Y, and Z positioning of the surgical end. The surgical end 320 may comprise an exemplary uterine manipulator arrangement as described below, comprising an extension arm with an end effector such as a uterine manipulator attached thereto (with or without a detachable interface therebetween), and means (e.g., as disclosed elsewhere herein) for fine positioning X,Y (up, down, left, right), in/out, and rotational (rotate counterclockwise, rotate clockwise) movement of the end effector responsive to user input from the control console. The exemplary robotic uterine manipulation system can perform initial operational checks, and upon successful completion of the check, can enter into an operational mode. A calibration procedure can be used to initiate all of the control elements to zero and remove stored, pre-set positions.

After the calibration process, the device table, which can house the surgical end, can be wheeled into the approximate operational position, locked into place, and then can be macro-positioned using the X,Y,Z controls of the device table. The X, Y, and Z-axis manipulators of the device table can facilitate the floating fulcrum of the surgical end to be positioned accurately at the inner zeros where all rotation can be centered around. The surgical end can be an electromechanical device by which the end effector can be moved translationally (along the X and Y axes and in/out) and rotationally (clockwise and counterclockwise), individually or simultaneously.

The user console 310 can be a control console as described above, which can facilitate operational interface to the user. The system can start in a "lock" state, which can be a safety state that may have to be switched off in order to initiate anatomical positioning. The system can be switched or otherwise provided into "lock" mode in the event of either user directive or inactivity timeout. Commands to move the end effector can be initiated via a joystick and rocker switch. X,Y translation and rotation can be controlled by a 3-axis joystick while in/out motion can be handled via a single access rocker switch. Most or all controls can be proportional such that the speed can be adjusted based on the amount of deflection of the control element. Upon completion of the surgery, the system can be removed from the operating room, cleaned, and put away for storage. The end effector may be reusable or disposable.

As shown in FIG. 3, the user console 310 can include a video screen, to facilitate viewing the surgical area by the surgeon. A central processing unit (CPU) can be connected to a joystick, which can be used to position the end effector, various buttons to control the end effector, and a display. The user console 310 can also include an emergency stop button, which can be connected to power, and to the surgical end mounting unit 318 via various wiring/interconnects. The surgical end mounting unit 318, which can be connected to the user console 310 via the wiring/interconnects, can have its own power button and emergency stop button. The surgical end mounting unit 318 can have various motor drivers, which can be used to adjust the X, Y, and Z axes of the end effector. The surgical end mounting unit 318 can be connected via wiring/interconnects to the surgical end 320, which can have a power button, various limit switches, and various motor drivers as needed. The motor drivers can control the X,Y axis, as well as the rotation and the in/out movement of the end effector.

First Exemplary Uterine Manipulator Arrangement

Figure 5:
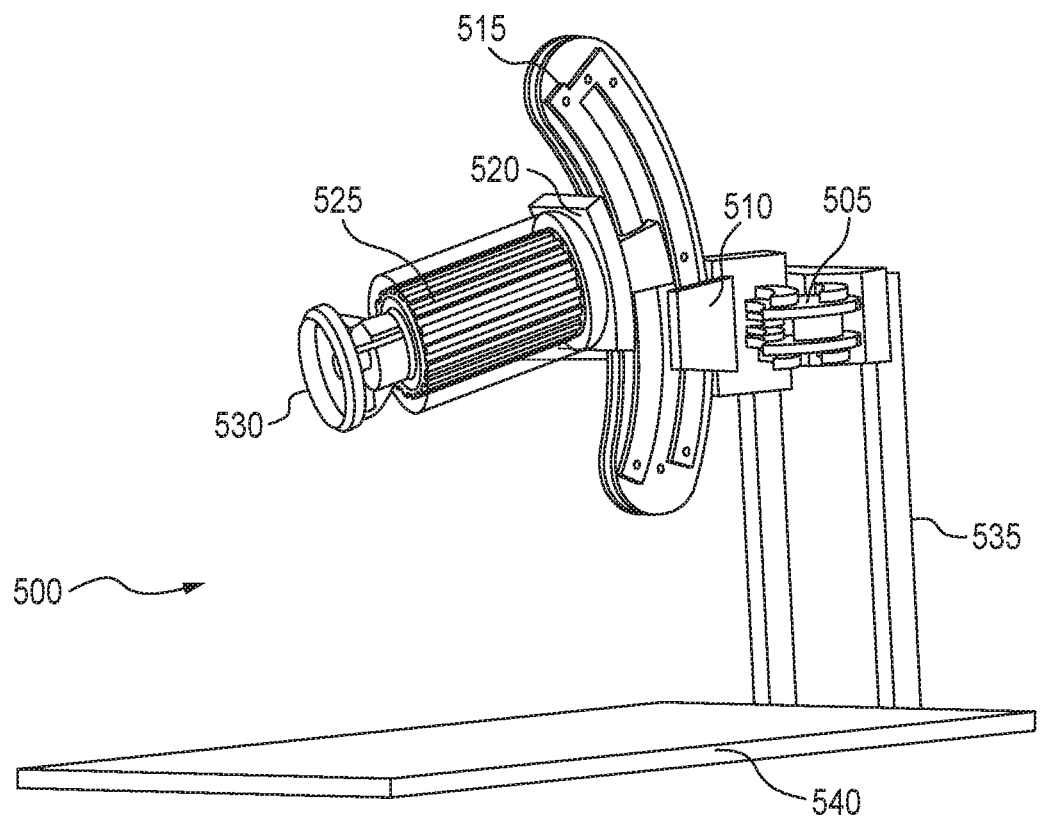
FIGS. 5-11C are schematic diagrams of an exemplary uterine manipulator arrangement, according to some embodiments.
Figure 6:
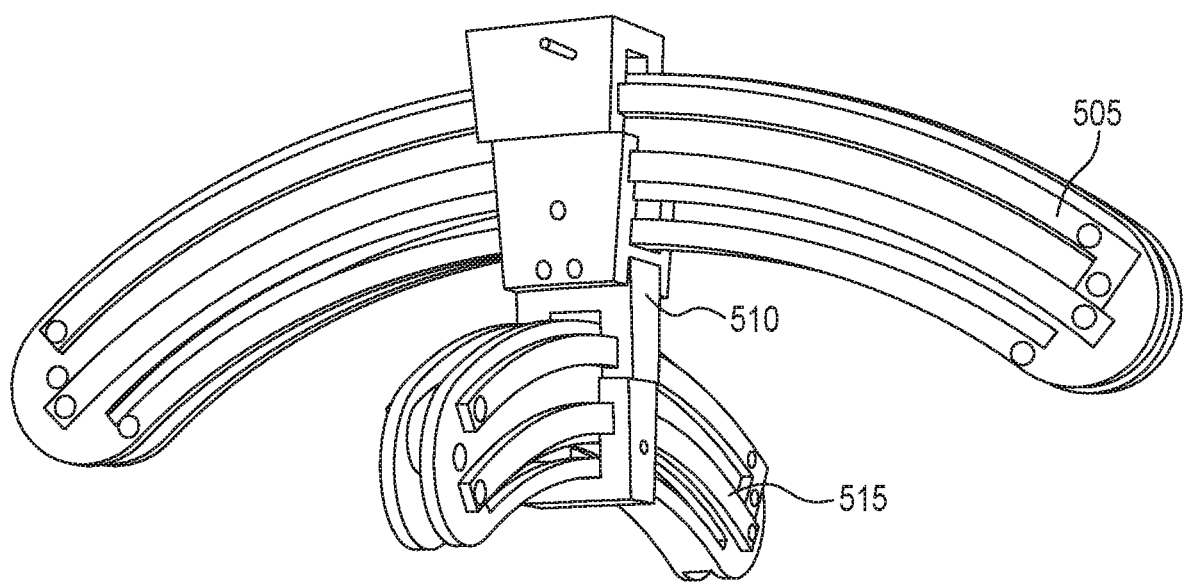

FIGS. 5-8 are schematic diagrams of a first exemplary uterine manipulator arrangement 500, according to some embodiments of the invention. As shown in FIG. 5, the exemplary uterine manipulator arrangement 500 can include a first portion 505, which can facilitate movement of a uterine manipulator 530 in a first direction along a track integrated within the first portion 505. First portion 505 can include a first connection arrangement 510, which can be used to connect second portion 515 to first portion 505. Second portion 515 can facilitate movement of the uterine manipulator 530 in a second direction, which can be different than the first direction, along a track integrated into second portion 515. Second portion 515 can include a second connection arrangement 520, which can be used to connect third portion 525 to second portion 515. Third portion 525 can facilitate an in/out and rotation movement of the uterine manipulator 530, which can include a colpotomy ring. First portion 505 can be connected to a stand 535, which can be connected to a base portion 540, which can support the entire structure, and which can be placed on a moveable or stationary table. FIG. 6 illustrates a close-up view of first portion 505, first connection arrangement 510, and second portion 515.

Figure 7:
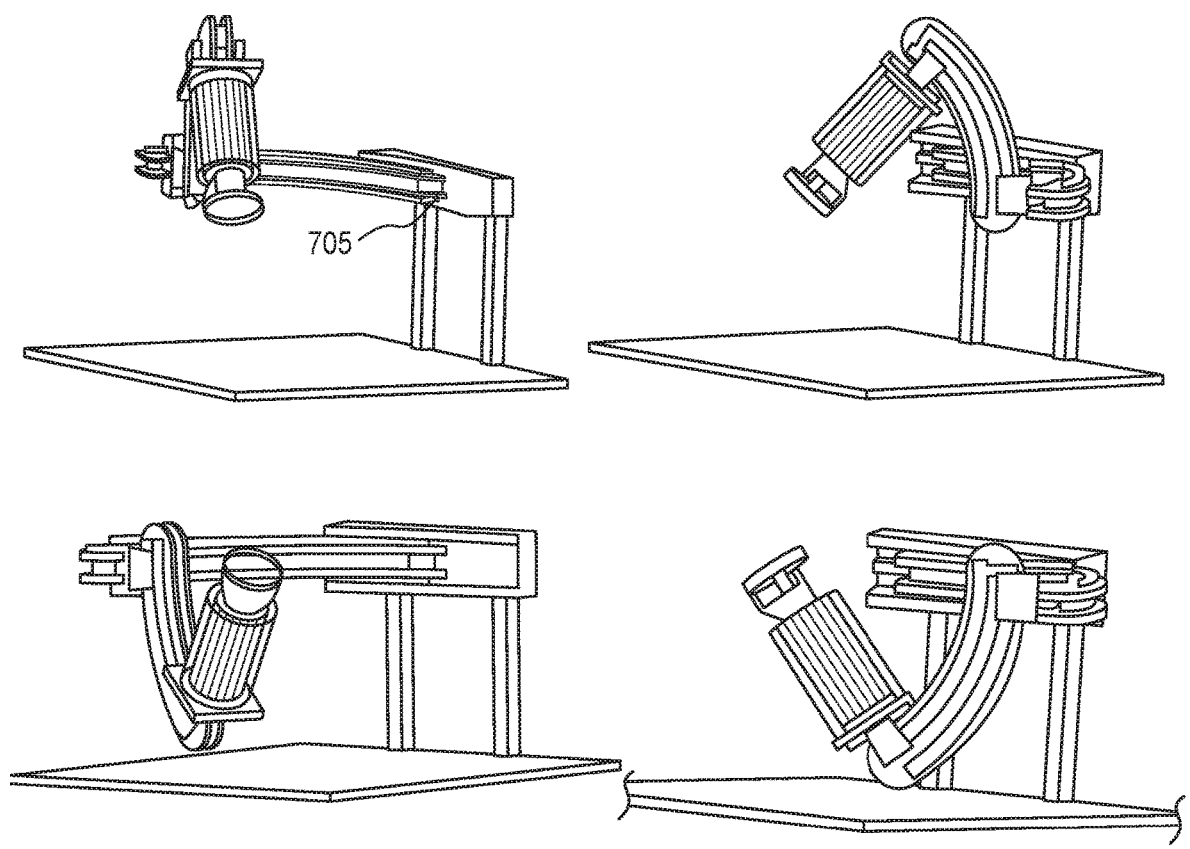

FIG. 7 illustrates the rotational motion of the exemplary uterine manipulator arrangement 500 provided by first portion 505 and second portion 515. For example, first portion 505 can be connected to stand 535 through a curved track 705. Curved track 705 can facilitate the rotational movement of first portion 505, which can facilitate the rotational movement of the entire uterine manipulator arrangement 500.

Figure 8A:
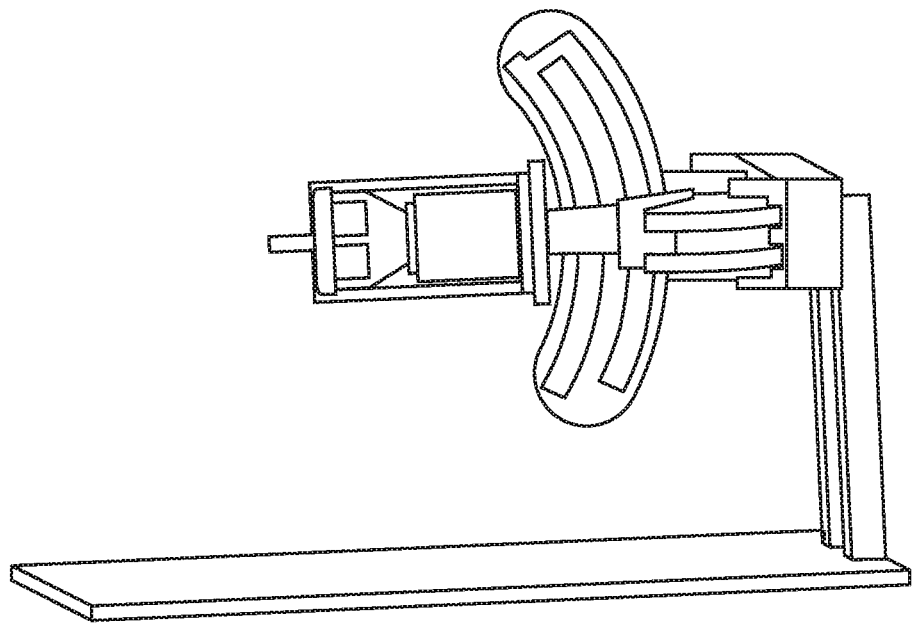
Figure 8B:
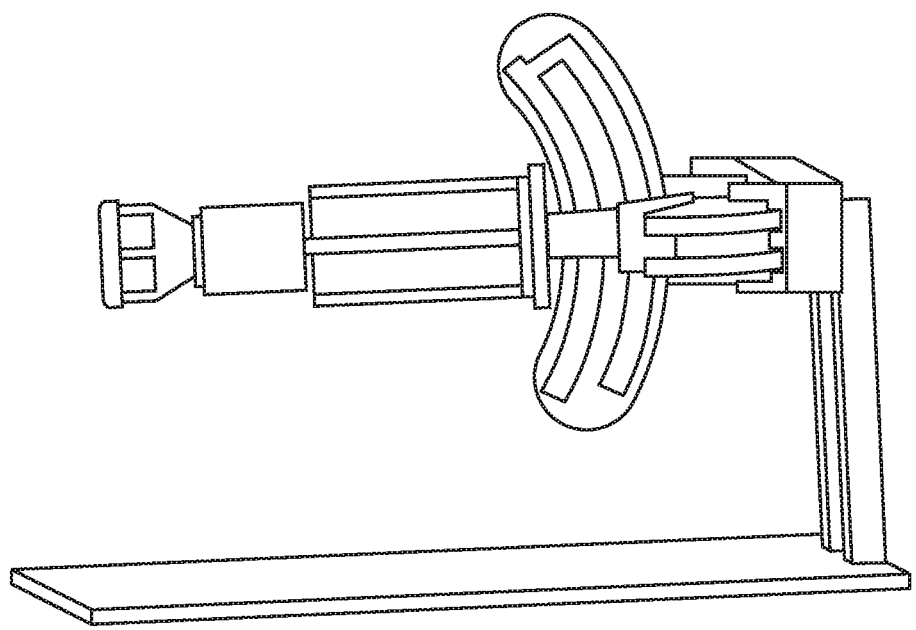

FIGS. 8A and 8B illustrate the translational range of motion of the exemplary uterine manipulator arrangement 500 provided by third portion 525. FIG. 8A shows third portion 525 in fully retracted form, and FIG. 8B shows third portion 525 in fully extended form. In some embodiments, the travel distance between the fully retracted and fully extended positions of third portion 525 is about 8 cm (about 3.14 inches).

Figure 9:
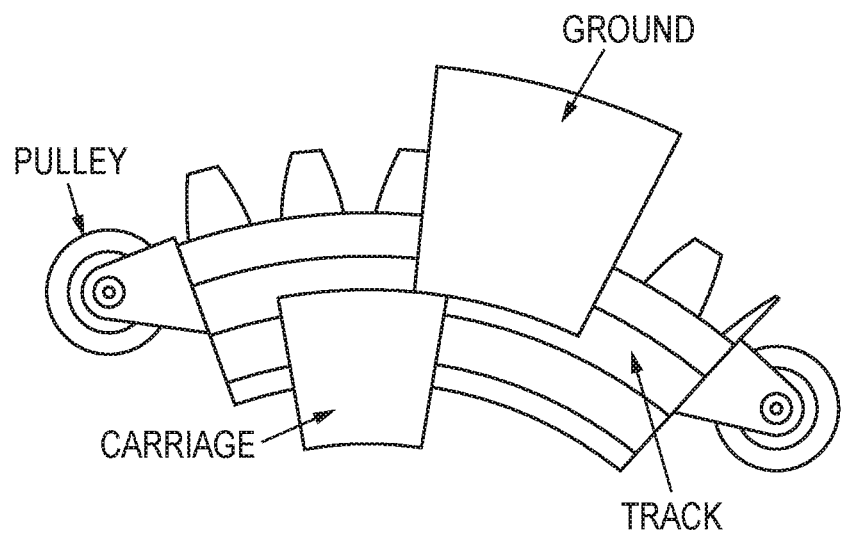

FIG. 9 is a schematic diagram illustrating the first and second degrees of freedom of the exemplary uterine manipulator arrangement 500 as provided by first portion 505 and second portion 515, according to some embodiments. A moving track and carriage provides the required range in half the size. Outside the track is a gear, and the motion of the gear (driven by a motor) is translated to the carriage through a cable. One actuator is provided for moving both the track and the carriage.

Figure 10:
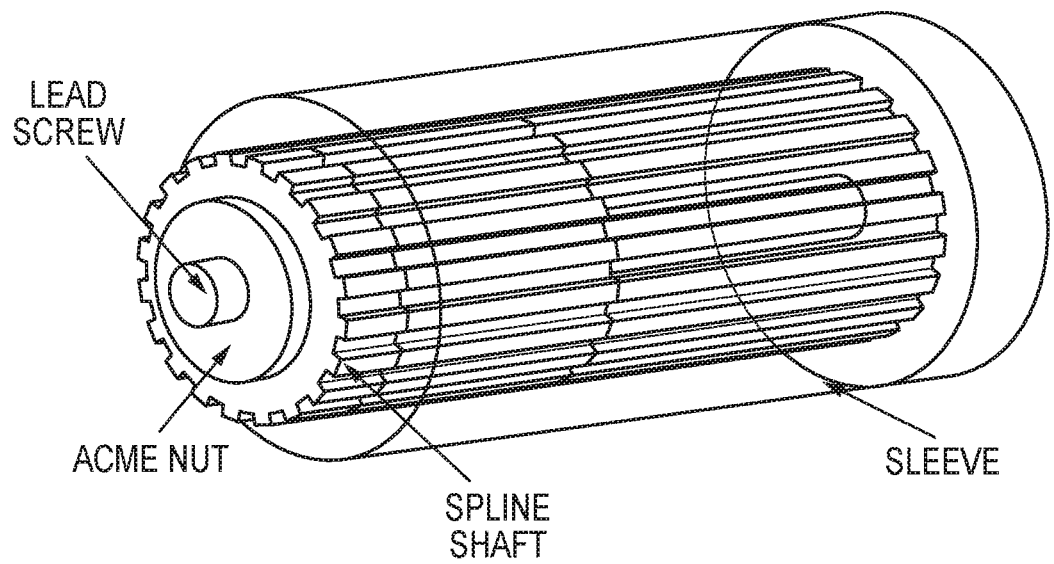

FIG. 10 is a schematic diagram illustrating the third and fourth degrees of freedom of the exemplary uterine manipulator arrangement 500 as provided by third portion 525, according to some embodiments. Translation is provided via a lead screw, and rotation is provided via a spline shaft and meshing sleeve. In some embodiments, the dimensions for third portion 525 are about 2 inches for the outer diameter and about 4.5 inches for the length.

Figure 11A:
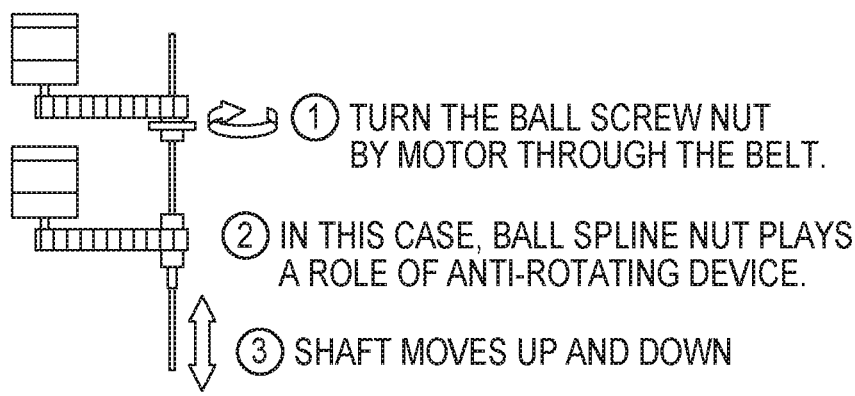
Figure 11B:
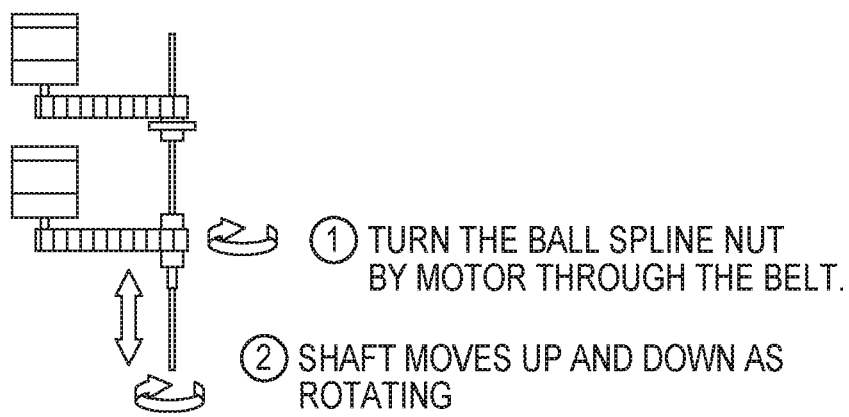
Figure 11C:
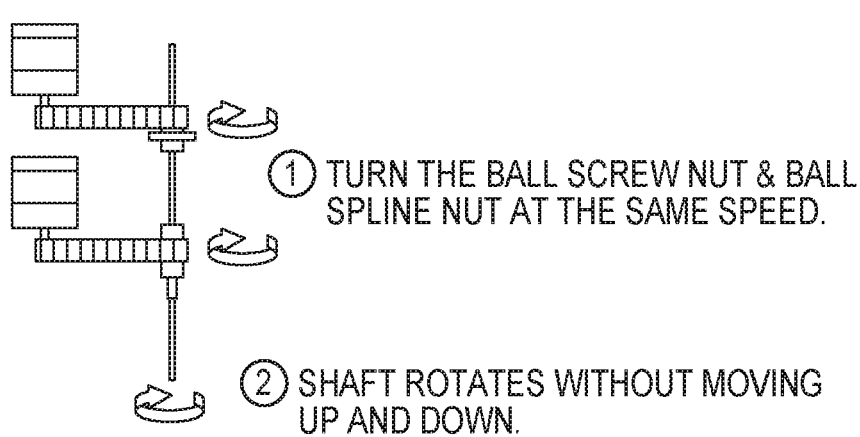

FIGS. 11A-11C are schematic diagrams illustrating exemplary operating principles of the exemplary uterine manipulator arrangement 500, according to some embodiments. FIG. 11A shows operating principles for linear translation. FIG. 11B shows operating principles for spiral motion. FIG. 11C shows operating principles for pure rotation.

Second Exemplary Uterine Manipulator Arrangement

Figure 12:
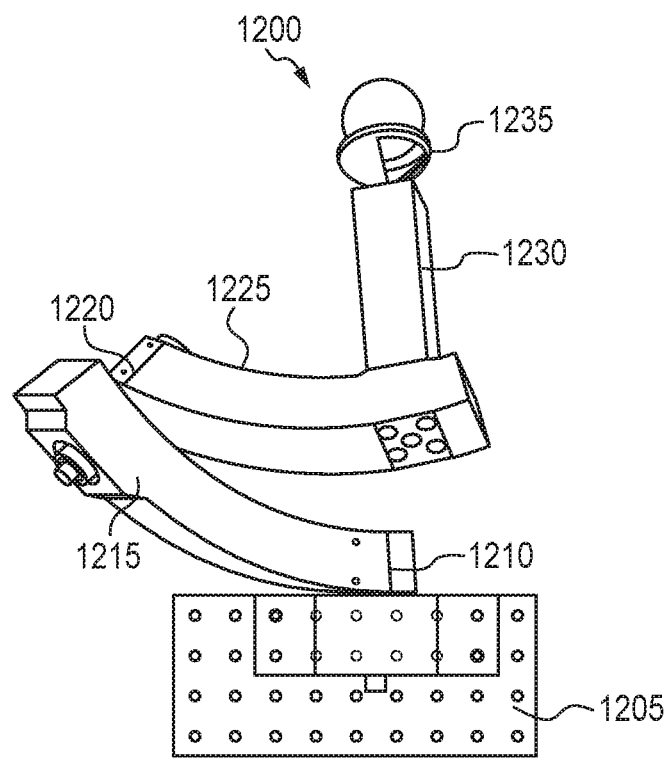
FIGS. 12-20B are schematic diagrams of another exemplary uterine manipulator arrangement, according to some embodiments.
Figure 13:
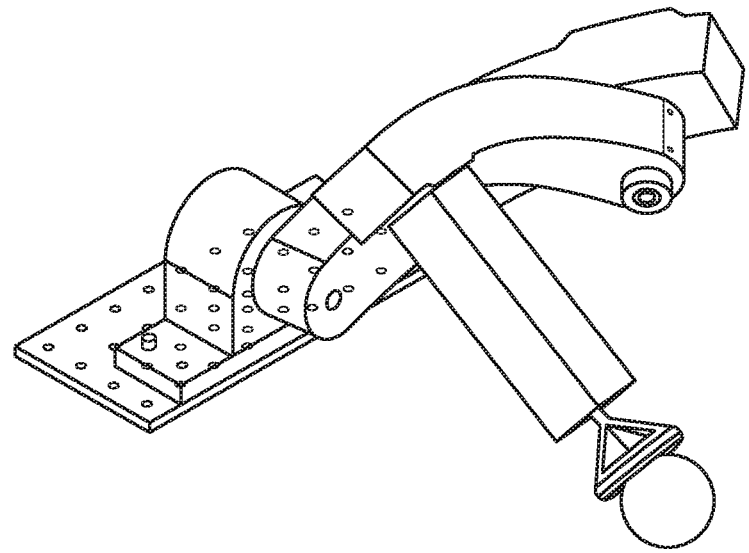
Figure 14:
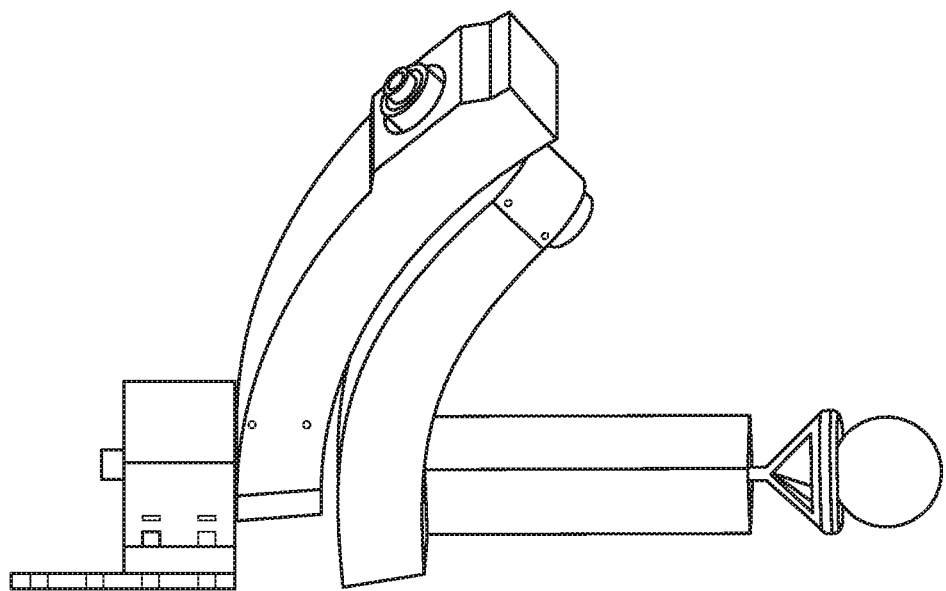
Figure 15:
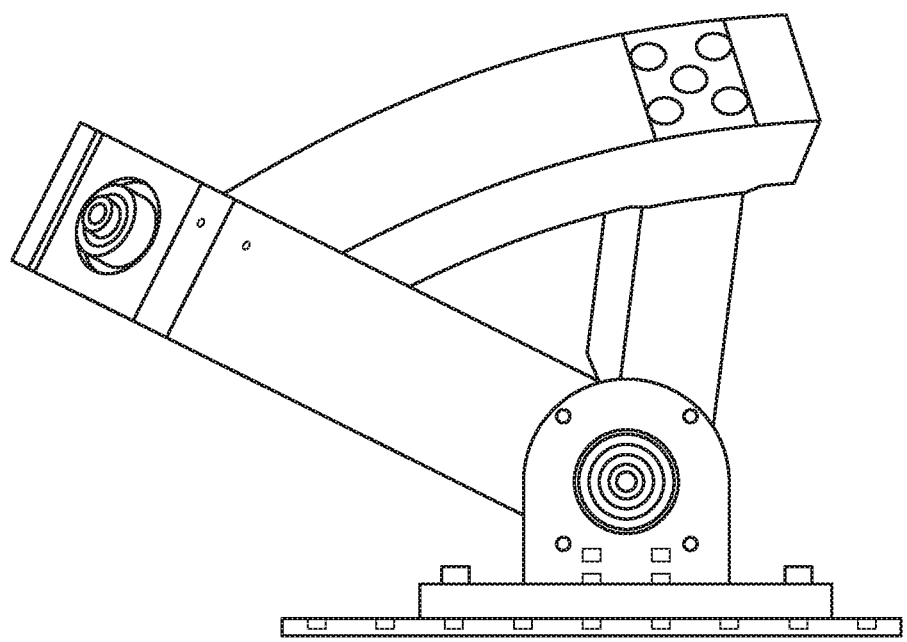
Figure 16:
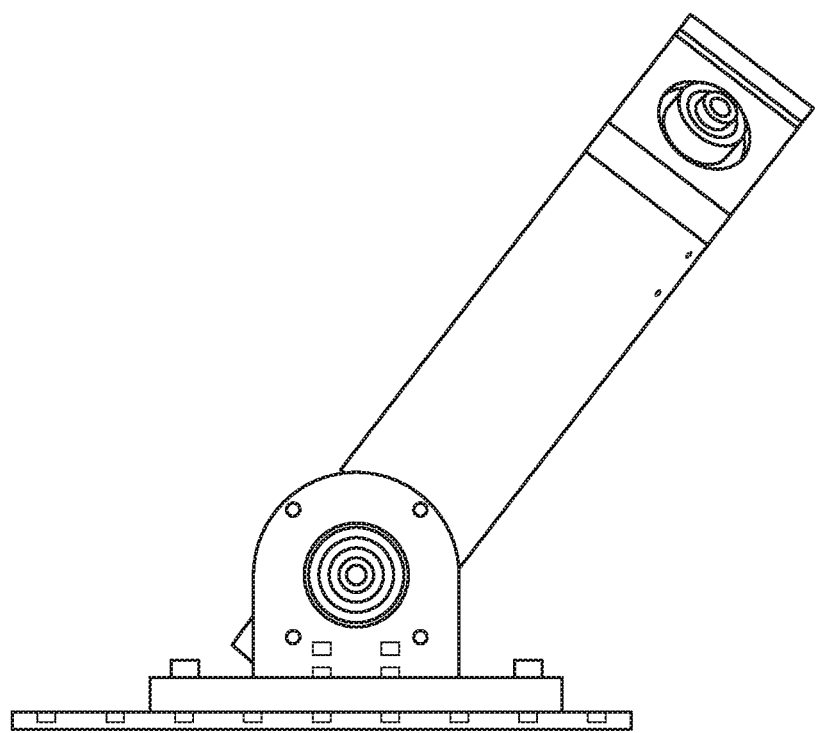
Figure 17:
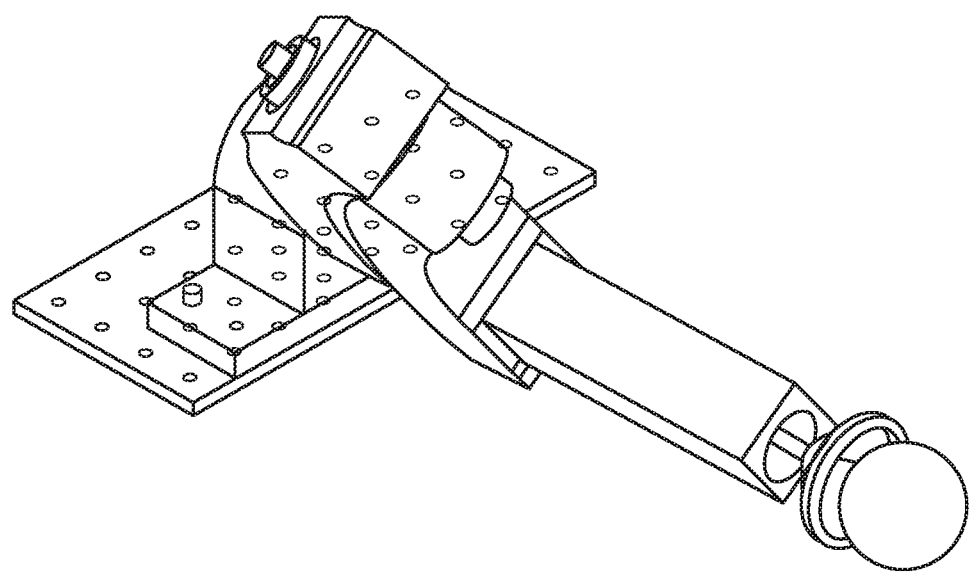
Figure 18:
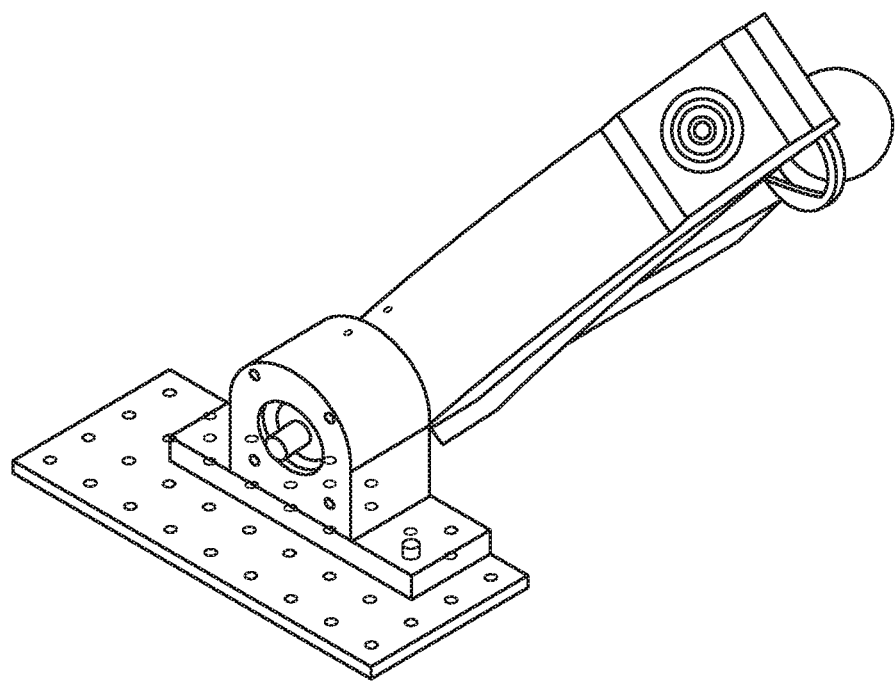
Figure 19:
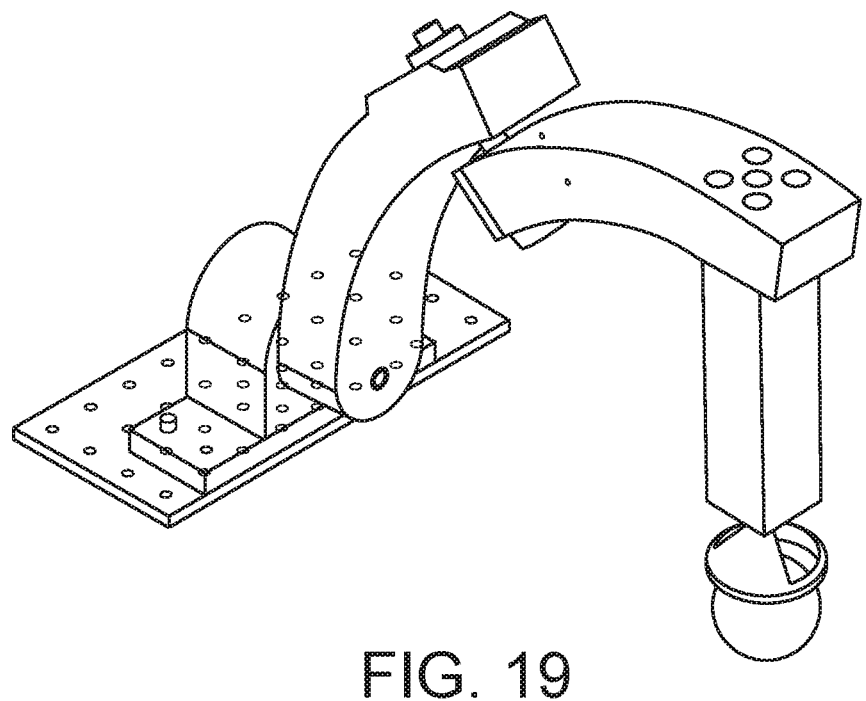

FIGS. 12-19 are schematic diagrams of a second exemplary uterine manipulator arrangement 1200, according to some embodiments of the invention. As shown in FIG. 12, uterine manipulator arrangement 1200 can include a base portion 1205, which can be connected to a first rotating portion 1215 through a first rotation or pivot point 1210. First rotating portion 1215 can facilitate a rotation of the entire uterine manipulator arrangement 1200. First rotating portion can be connected to a second rotating portion 1225 through a second rotation or pivot point 1220. Second rotating portion 1225 can facilitate a rotation of a part of the exemplary uterine manipulator arrangement 1200. Second rotating portion can be connected to arm 1230, which can facilitate an in/out and rotation movement of the uterine manipulator 1235, which can include a colpotomy ring.

FIGS. 13-19 are schematic diagrams illustrating the spherical motion of the exemplary uterine manipulator arrangement 1200. For example, due to the arrangement of rotational joints 1210 and 1220 in the exemplary uterine manipulator arrangement 1200, the uterine manipulator 1235 can traverse a path that can circumscribe a sphere, thus avoiding any unwanted penetration within the body. Such an exemplary arrangement can facilitate a very large range of angular motion through which the uterine manipulator 1235 can traverse.

Figure 20A:
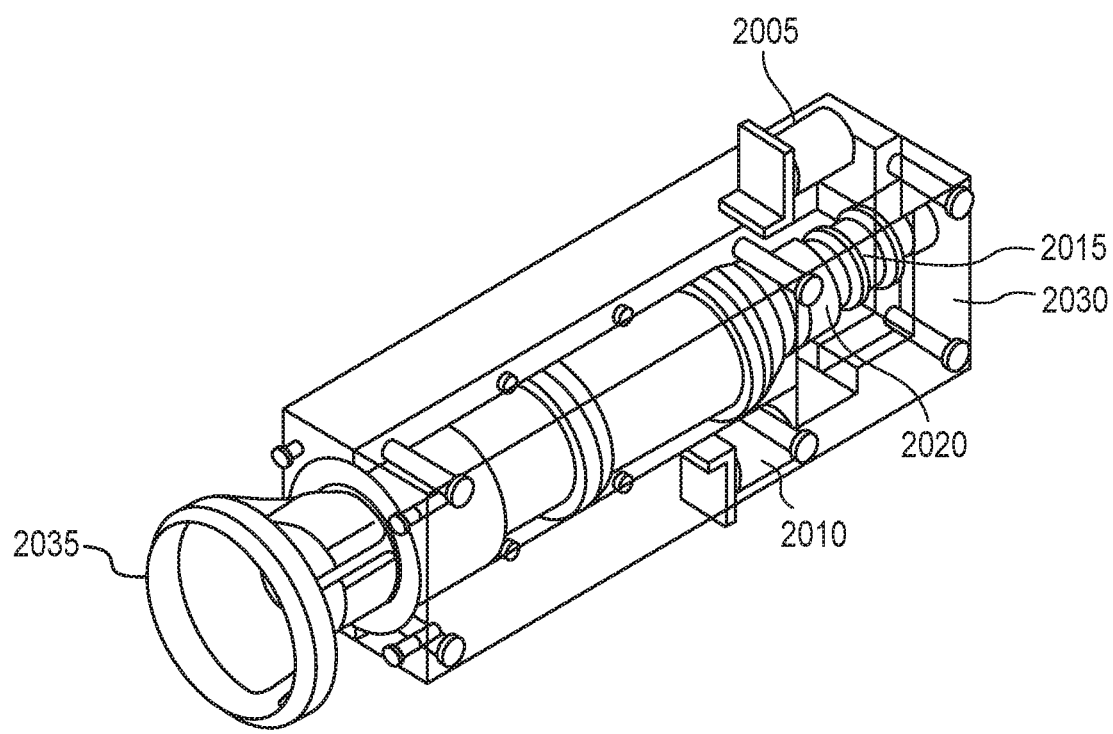
Figure 20B:
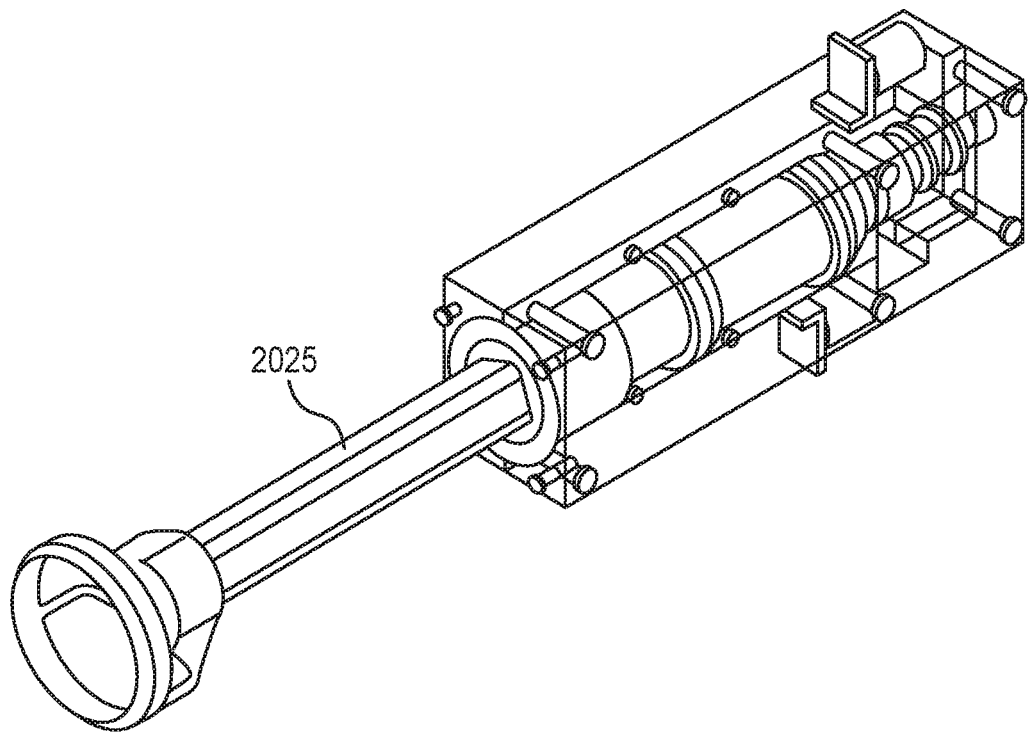

FIGS. 20A and 20B are diagrams of the third portion 1230 of the exemplary uterine manipulator arrangement 1200, according to some embodiments of the invention. FIG. 20A shows the third portion 2030 and the uterine manipulator 2035 in a non-extended, non-rotated position. Upon the action of motors 2005 and 2010 on pulleys 2015 and 2020, the arm 2025 can extend, rotate, or both extend and rotate.

Exemplary Device Table

Figure 21:
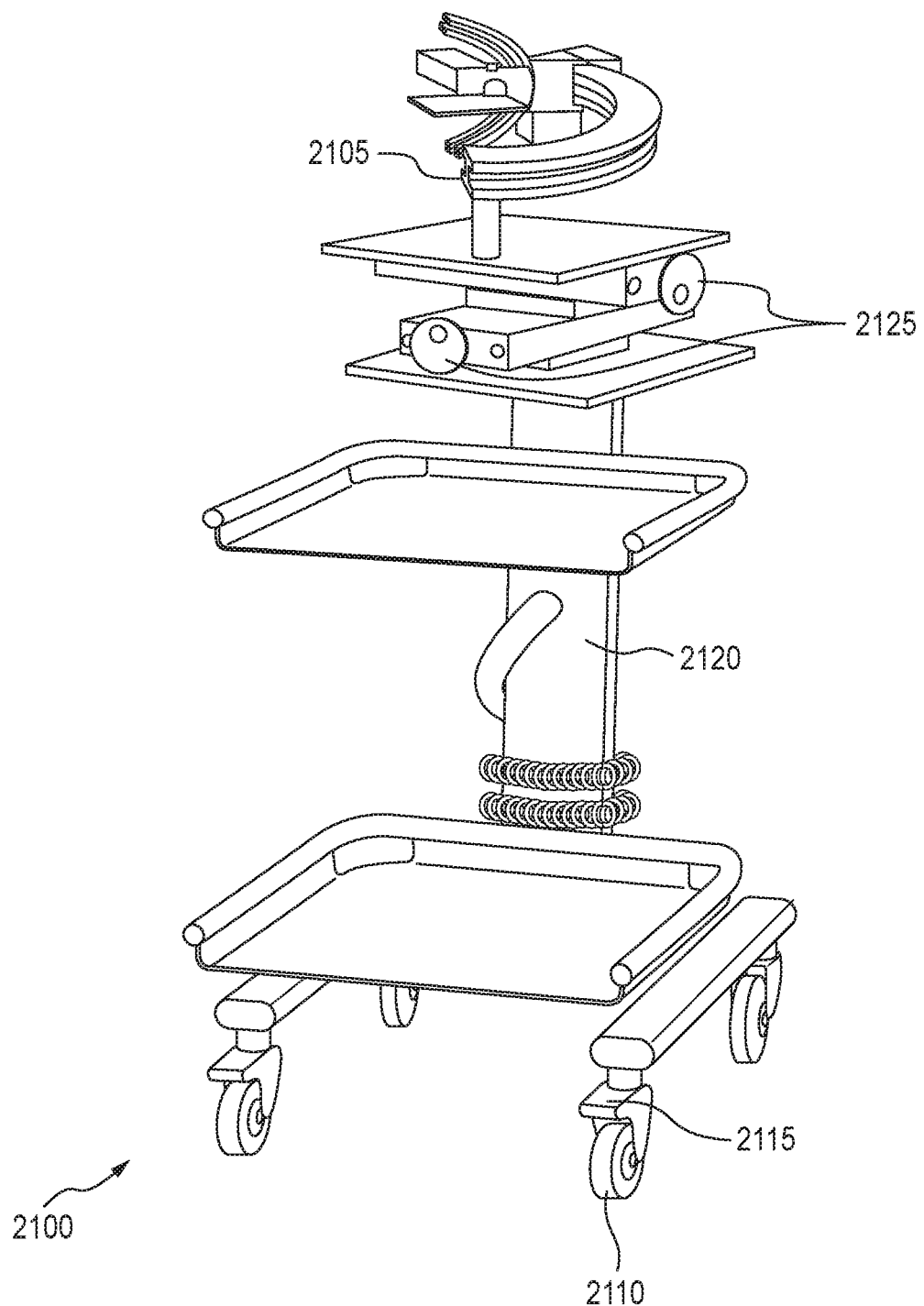
FIG. 21 is a schematic diagram of an exemplary device table, according to some embodiments, with an exemplary uterine manipulator arrangement mounted thereto.

FIG. 21 shows an exemplary device table comprising portable structure 2100 that can provide a mobile base for an exemplary uterine manipulator arrangement 2105, according to some embodiments of the invention. As shown in FIG. 21, the portable structure 2100 can be provided on wheels 2110, which can be locked in place using wheel locks 2115. Vertical (Z-axis) positioning can be achieved using a structure 2120, and X,Y positioning can be achieved using structures 2125.

Exemplary Operation

Figure 22:
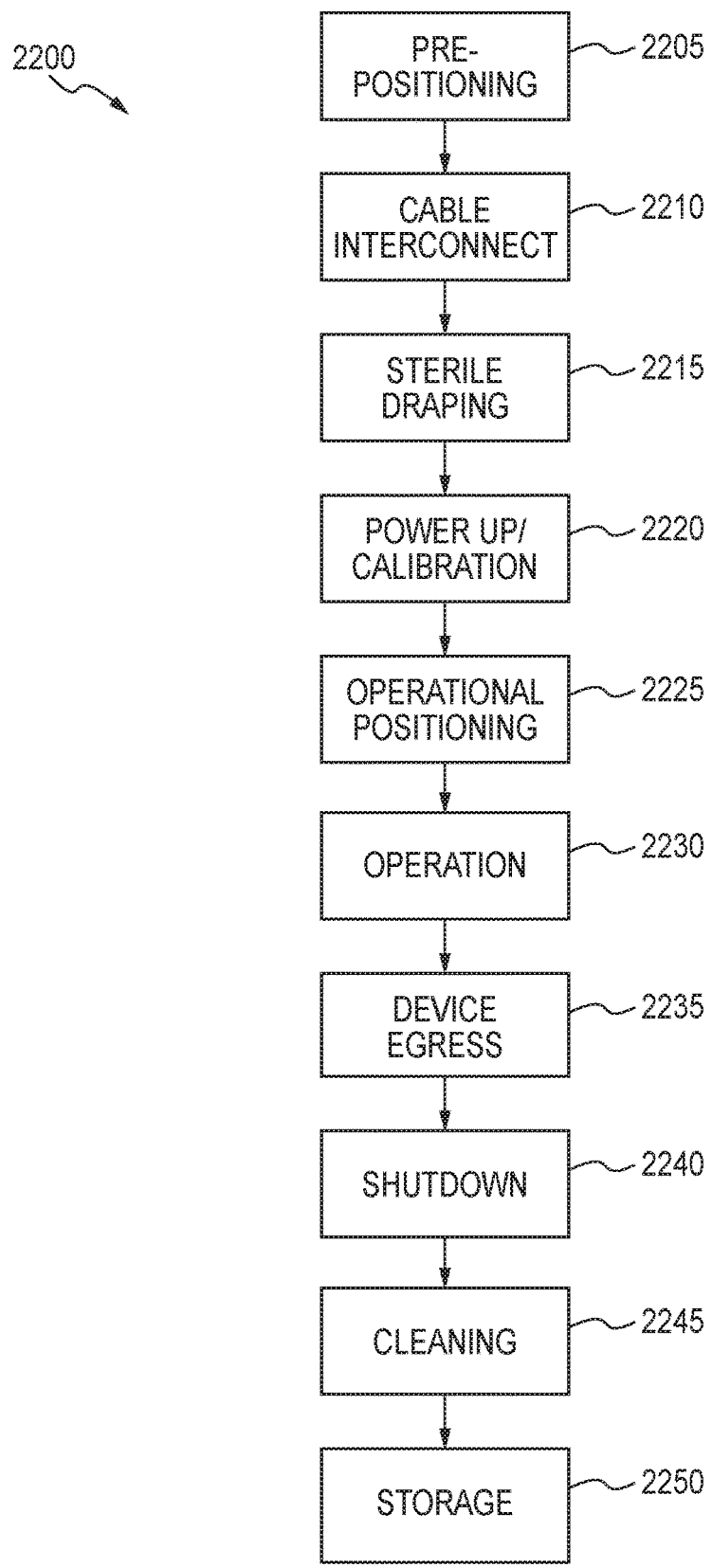
FIG. 22 is a flow diagram of an exemplary method for using a robotic uterine manipulation system of the present invention, according to some embodiments.

FIG. 22 shows a flow diagram of an exemplary method 2200 for performing a laparoscopic surgery using an exemplary uterine manipulator arrangement of the present invention. For example, at procedure 2205, pre-positioning of the exemplary uterine manipulator arrangement can be performed. Cables can be connected to the uterine manipulator arrangement at procedure 2210, and a sterile drape can be applied at procedure 2215. At procedure 2220, the exemplary uterine manipulator arrangement can be powered up and calibrated, and operational positioning of the exemplary uterine manipulator arrangement can be performed at procedure 2225. An operation using the exemplary uterine manipulator arrangement can be performed at procedure 2230, and the uterine manipulator arrangement can be removed at procedure 2235. At procedure 2240, the exemplary uterine manipulator arrangement can be powered down, and then cleaned at procedure 2245 and stored for later use at procedure 2250.

Figure 23:
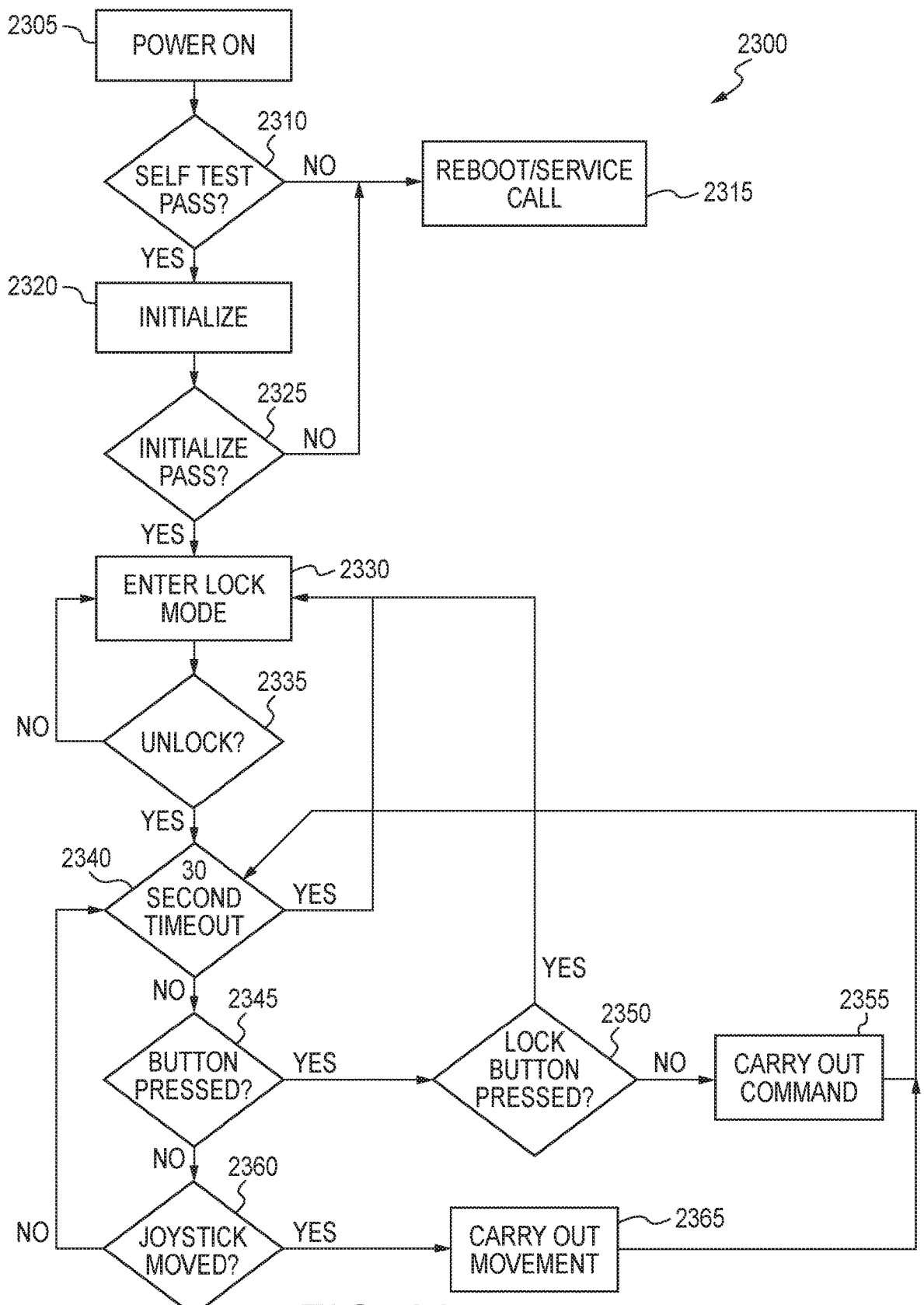
FIG. 23 is a flow diagram of another exemplary method for using a robotic uterine manipulation system of the present invention, according to some embodiments.

FIG. 23 shows a flow diagram of another exemplary method 2300 for using an exemplary uterine manipulator arrangement of the present invention, according some embodiments. For example, at procedure 2305, the uterine manipulator arrangement can be powered on, and a self-test can be performed at procedure 2310. If the uterine manipulator arrangement does not pass the self-test, then the uterine manipulator arrangement can either be rebooted, or a service call can be made, at procedure 2315. If the self-test is passed, an initialization procedure can be initiated at procedure 2320. At procedure 2325, if the uterine manipulator arrangement does not initialize, then the uterine manipulator arrangement can either be rebooted, or a service call can be made, at procedure 2315. If the uterine manipulator arrangement does initialize, then a lock mode can be entered at procedure 2330. At procedure 2335, if the uterine manipulator arrangement is not unlocked, then the uterine manipulator arrangement can remain in lock mode. If the uterine manipulator arrangement is unlocked, then a timer (e.g., a 30 second timer) can be initiated at procedure 2340. If the timer reaches zero, then lock mode can be entered into again at procedure 2330. If the timer does not reach zero, then a determination of a button press can be performed at procedure 2345. If there is a button press at procedure 2345, a determination can be made as to whether the button press was a lock button press at procedure 2350, and if so, then the exemplary uterine manipulator arrangement can be locked at procedure 2330. If a different button (not the lock button) is pressed, then a command associated with the button can be carried out at procedure 2355. If there is no button press at procedure 2345, but there is a joystick movement at procedure 2360, then the movement corresponding to the joystick can be carried out at procedure 2365. If there is no button press at procedure 2345, and no joystick movement at procedure 2360, then a timer can be initiated at procedure 2340.

Figure 24:
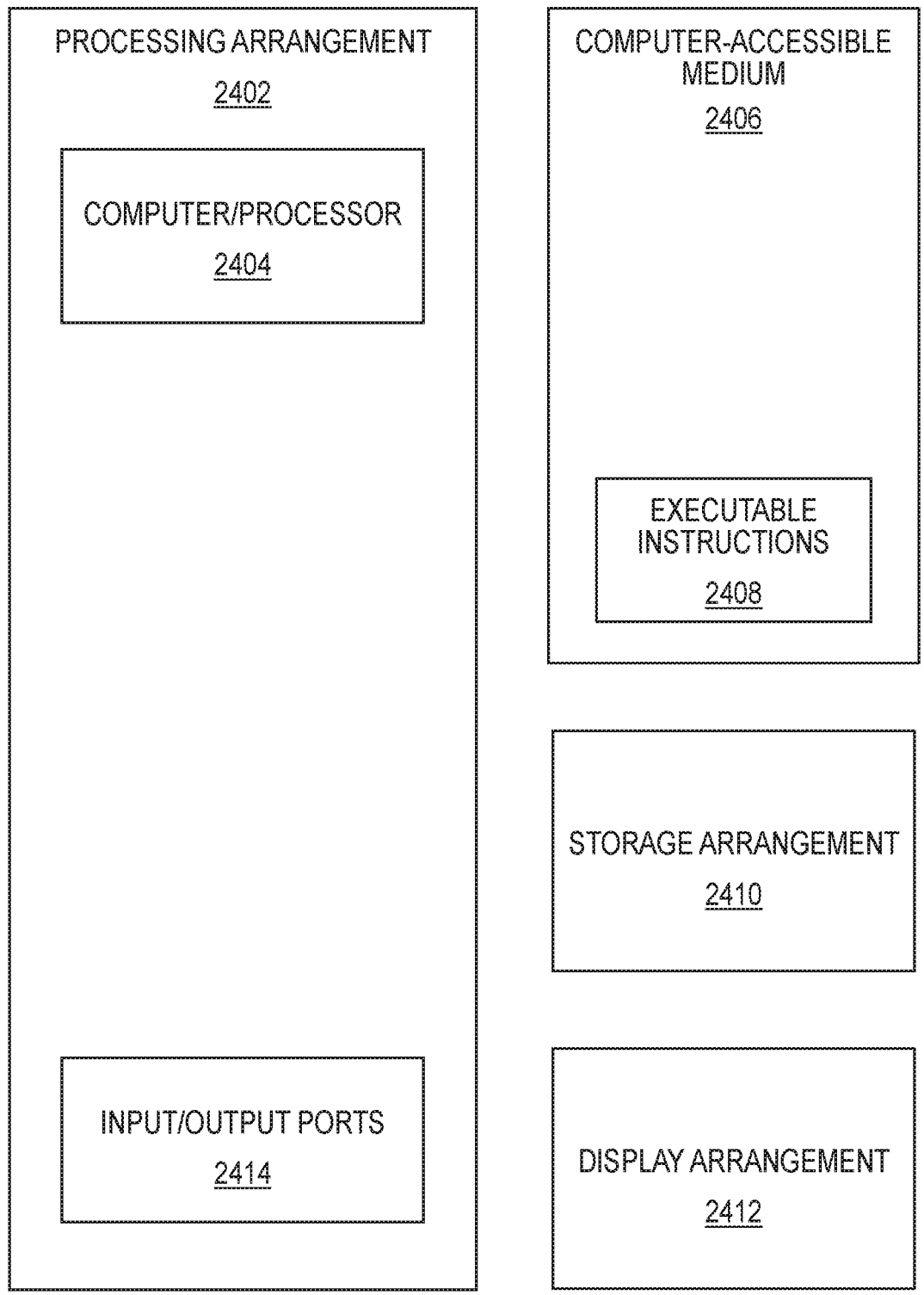
FIG. 24 is block diagram of an exemplary computer system, according to some embodiments.

FIG. 24 shows a block diagram of an exemplary embodiment of a system according to some embodiments of the invention. For example, exemplary procedures in accordance with the present invention can be performed by a processing arrangement and/or a computing arrangement 2402. Such processing/computing arrangement 2402 can be, for example, entirely or a part of, or can include, a computer/processor 2404 that can include, for example, one or more microprocessors, and use instructions stored on a computer-accessible medium (e.g., RAM, ROM, hard drive, or other storage device).

As shown in FIG. 24, a computer-accessible medium 2406 (e.g., as described herein above, a storage device such as a hard disk, floppy disk, memory stick, CD-ROM, RAM, ROM, etc., or a collection thereof) can be provided (e.g., in communication with the processing arrangement 2402). The computer-accessible medium 2406 can contain executable instructions 2408 thereon for providing the functionality herein. In addition or alternatively, a storage arrangement 2410 can be provided separately from the computer-accessible medium 2406, which can provide the instructions to the processing arrangement 2402 so as to configure the processing arrangement to execute certain exemplary procedures, processes and methods, as described herein above, for example.

Further, the exemplary processing arrangement 2402 can be provided with or include an input/output arrangement 2414, which can include, for example a wired network, a wireless network, the internet, an intranet, a data collection probe, a sensor, etc. As shown in FIG. 24, the exemplary processing arrangement 2402 can be in communication with an exemplary display arrangement 2412, which, according to some embodiments, can be a touch-screen configured for inputting information to the processing arrangement in addition to outputting information from the processing arrangement, for example. Further, the exemplary display 2412 and/or a storage arrangement 2410 can be used to display and/or store data in a user-accessible format and/or user-readable format.

While there have been shown and described fundamental novel features of the invention as applied to the preferred and exemplary embodiments thereof, it will be understood that omissions and substitutions and changes in the form and details of the disclosed invention may be made by those skilled in the art without departing from the spirit of the invention. Moreover, as is readily apparent, numerous modifications and changes may readily occur to those skilled in the art. For example, any feature(s) in one or more embodiments may be applicable and combined with one or more other embodiments. Hence, it is not desired to limit the invention to the exact construction and operation shown and described and, accordingly, all suitable modification equivalents may be resorted to falling within the scope of the invention as claimed. It is the intention, therefore, to be limited only as indicated by the scope of the claims appended hereto.

What is claimed is:

1. A robotic anatomical manipulation system for use with an end effector configured to position and hold an anatomy of a patient during a minimally invasive surgical procedure, the system comprising:
   a remote machine comprising:
      a base comprising a mobile base having one or more lockable casters or a mountable base configured to be mounted to a surgical table; and
      a moveable extension arm connected to the base, the extension arm having a distal end positionable relative to the surgical table and configured to connect to the end effector; and
   a control console in communication with the remote machine via a wired connection or a wireless connection,
   the extension arm consisting essentially of two linear segments, one proximal and one distal, a first $\Psi$ rotation joint and a first $\Phi$ rotation joint at a proximal end of the proximal segment connected to the base, a second $\Phi$ rotation joint between the proximal and distal segments, a second $\Psi$ rotation joint and a third $\Phi$ rotation joint at a distal end of the distal segment, and a $\Theta$ rotation joint and a translation extension joint connected thereto,
   wherein the three $\Phi$ rotation joints, two $\Psi$ rotation joints, one $\Theta$ rotation joint, and one translation extension joint are configured to provide articulation used during the surgical procedure to move the end effector to manipulate the patient's anatomy responsive to user input received from the control console via the wired connection or the wireless connection, and wherein the end effector movement includes translational movement up, down, left, right, in and out, and rotational movement counterclockwise and clockwise.

2. The system of claim 1, wherein the remote machine comprises the mobile base having the one or more lockable casters, the mobile base including a bumper bar around a perimeter thereof, the bumper bar positionable between the mobile base and the surgical table and configured to be raised and lowered to lock and unlock the casters.

3. The system of claim 1, further comprising an interface connected to the distal end of the extension arm, the interface configured to connect the $\Theta$ rotation joint and the translation extension joint to the end effector.

4. The system of claim 3, wherein the interface is configured to connect the $\Theta$ rotation joint and the translation extension joint to a uterine manipulator configured to position and hold the patient's uterus during a robotically-assisted or manual laparoscopic hysterectomy.

5. The system of claim 1, further comprising a disposable sterile drape covering the remote machine and maintaining a sterile field between the remote machine and the patient.

6. The system of claim 1, wherein the remote machine further comprises one or more sensors, and wherein the remote machine is configured to transmit sensor data and information to the control console via the wired connection or the wireless connection.

7. The system of claim 6, wherein the remote machine is configured to determine via the one or more sensors an amount of force applied to a working end.

8. The system of claim 7, wherein the remote machine is configured to provide a warning when the force is determined to exceed a predetermined threshold.

9. The system of claim 7, wherein the remote machine is configured to automatically stop when the force is determined to exceed a predetermined threshold.

10. A robotic anatomical manipulation system for use with an end effector configured to position and hold an anatomy of a patient during a minimally invasive surgical procedure, the system comprising:
   a remote machine comprising:
      a base comprising a mobile base having one or more lockable casters or a mountable base configured to be mounted to a surgical table; and
      a moveable extension arm connected to the base, the extension arm having a distal end positionable relative to the surgical table and configured to connect to the end effector; and
   a control console in communication with the remote machine via a wired connection or a wireless connection,
   wherein the extension arm comprises two linear segments comprising a proximal segment and a distal segment, a first $\Psi$ rotation joint and a first $\Phi$ rotation joint at a proximal end of the proximal segment connected to the base, a second $\Phi$ rotation joint between the proximal and distal segments, a second $\Psi$ rotation joint and a third $\Phi$ rotation joint at a distal end of the distal segment, and a $\Theta$ rotation joint and a translation extension joint connected to the end effector,
   wherein the three $\Phi$ rotation joints, two $\Psi$ rotation joints, one $\Theta$ rotation joint, and one translation extension joint are configured to provide articulation used during the surgical procedure to move the end effector to manipulate the patient's anatomy responsive to user input received from the control console via the wired connection or the wireless connection, and wherein the end effector movement includes translational movement up, down, left, right, in and out, and rotational movement counterclockwise and clockwise, wherein the remote machine comprises the mobile base having the one or more lockable casters, the mobile base including a bumper bar around the entire perimeter thereof, the bumper bar positionable between the mobile base and the surgical table and configured to be raised and lowered to lock and unlock the casters.

11. The system of claim 10, further comprising an interface connected to the distal end of the extension arm, the interface configured to connect the Θ rotation joint and the translation extension joint to the end effector.

12. The system of claim 11, wherein the interface is configured to connect the Θ rotation joint and the translation extension joint to a uterine manipulator configured to position and hold the patient's uterus during a robotically-assisted or manual laparoscopic hysterectomy.

13. The system of claim 10, further comprising a disposable sterile drape covering the remote machine and maintaining a sterile field between the remote machine and the patient.

14. The system of claim 10, wherein the remote machine further comprises one or more sensors, and wherein the remote machine is configured to transmit sensor data and information to the control console via the wired connection or the wireless connection.

15. The system of claim 14, wherein the remote machine is configured to determine via the one or more sensors an amount of force applied to a working end.

16. The system of claim 15, wherein the remote machine is configured to provide a warning when the force is determined to exceed a predetermined threshold.

17. The system of claim 15, wherein the remote machine is configured to automatically stop when the force is determined to exceed a predetermined threshold.

* * * * *